(12) United States Patent
Wariar et al.

(10) Patent No.: US 8,888,710 B2
(45) Date of Patent: Nov. 18, 2014

(54) SYSTEM AND METHOD FOR ASSESSING CARDIAC PERFORMANCE THROUGH CARDIAC VIBRATION MONITORING

(75) Inventors: Ramesh Wariar, Blaine, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 559 days.

(21) Appl. No.: 13/208,722

(22) Filed: Aug. 12, 2011

(65) Prior Publication Data

US 2011/0301473 A1    Dec. 8, 2011

Related U.S. Application Data

(60) Division of application No. 11/367,852, filed on Mar. 3, 2006, now Pat. No. 8,025,624, which is a continuation-in-part of application No. 10/782,642, filed on Feb. 19, 2004, now Pat. No. 7,488,290.

(51) Int. Cl.
*A61B 5/02* (2006.01)
*A61B 7/04* (2006.01)

(52) U.S. Cl.
CPC ........................................ *A61B 7/04* (2013.01)
USPC ........... 600/528; 600/481; 600/508; 600/509; 600/527

(58) Field of Classification Search
USPC .................. 600/481, 300, 483, 485, 528, 508
See application file for complete search history.

(56) References Cited

U.S. PATENT DOCUMENTS

| | | |
|---|---|---|
| 3,298,362 A | 1/1967 | Lippitt et al. |
| 3,776,221 A | 12/1973 | McIntyre |
| 3,837,339 A | 9/1974 | Aisenberg et al. |
| 4,142,533 A | 3/1979 | Brownlee et al. |
| 4,197,856 A | 4/1980 | Northrop |
| 4,531,527 A | 7/1985 | Reinhold, Jr. et al. |
| 4,548,211 A | 10/1985 | Marks |

(Continued)

FOREIGN PATENT DOCUMENTS

| | | |
|---|---|---|
| EP | 0 34 2859 | 11/1989 |
| EP | 0 513 457 | 11/1992 |

(Continued)

OTHER PUBLICATIONS

Auer et al., "Paced Epimyocardial Electrograms for Noninvasive Rejection Monitoring After Heart Transplantation," The Journal of Heart and Lung Transplantation, vol. 15, No. 10, pp. 993-998 (Oct. 1996).

(Continued)

*Primary Examiner* — Michael D'Angelo
(74) *Attorney, Agent, or Firm* — Pauly, DeVries Smith & Deffner LLC

(57) ABSTRACT

A system and method for assessing cardiac performance through cardiac vibration monitoring is described. Cardiac vibration measures are directly collected through an implantable medical device. Cardiac events including at least one first heart sound reflected by the cardiac vibration measures are identified. The first heart sound is correlated to cardiac dimensional measures relative to performance of an intrathoracic pressure maneuver. The cardiac dimensional measures are grouped into at least one measures set corresponding to a temporal phase of the intrathoracic pressure maneuver. The at least one cardiac dimensional measures set is evaluated against a cardiac dimensional trend for the corresponding intrathoracic pressure maneuver temporal phase to represent cardiac performance.

19 Claims, 16 Drawing Sheets

(56) References Cited

U.S. PATENT DOCUMENTS

| | | |
|---|---|---|
| 4,686,999 A | 8/1987 | Snyder et al. |
| 4,750,495 A | 6/1988 | Moore et al. |
| 4,803,625 A | 2/1989 | Fu et al. |
| 4,809,697 A | 3/1989 | Causey, III et al. |
| 4,852,570 A | 8/1989 | Levine |
| 4,899,758 A | 2/1990 | Finkelstein et al. |
| 4,958,645 A | 9/1990 | Cadell et al. |
| 4,974,607 A | 12/1990 | Miwa |
| 4,987,897 A | 1/1991 | Funke |
| 5,003,976 A | 4/1991 | Alt |
| 5,040,536 A | 8/1991 | Riff |
| 5,085,213 A | 2/1992 | Cohen |
| 5,113,859 A | 5/1992 | Funke |
| 5,113,869 A | 5/1992 | Nappholz et al. |
| 5,133,346 A | 7/1992 | Kulkarni |
| H1114 H | 12/1992 | Schweitzer et al. |
| 5,199,428 A | 4/1993 | Obel et al. |
| 5,291,895 A | 3/1994 | McIntyre |
| 5,301,105 A | 4/1994 | Cummings, Jr. |
| RE34,663 E | 7/1994 | Seale |
| 5,331,549 A | 7/1994 | Crawford, Jr. |
| 5,333,615 A | 8/1994 | Craelius et al. |
| 5,336,245 A | 8/1994 | Adams et al. |
| 5,355,889 A | 10/1994 | Nevo et al. |
| 5,357,427 A | 10/1994 | Langen et al. |
| 5,390,238 A | 2/1995 | Kirk et al. |
| 5,416,695 A | 5/1995 | Stutman et al. |
| 5,421,343 A | 6/1995 | Feng |
| 5,437,278 A | 8/1995 | Wilk |
| 5,438,983 A | 8/1995 | Falcone |
| 5,464,012 A | 11/1995 | Falcone |
| 5,522,860 A | 6/1996 | Molin et al. |
| 5,544,661 A | 8/1996 | Davis et al. |
| 5,553,609 A | 9/1996 | Chen et al. |
| 5,557,514 A | 9/1996 | Seare et al. |
| 5,576,952 A | 11/1996 | Stutman |
| 5,584,868 A | 12/1996 | Salo et al. |
| 5,591,215 A | 1/1997 | Greenhut et al. |
| 5,603,331 A | 2/1997 | Heemels et al. |
| 5,660,183 A | 8/1997 | Chiang et al. |
| 5,673,691 A | 10/1997 | Abrams et al. |
| 5,687,734 A | 11/1997 | Dempsey et al. |
| 5,697,959 A | 12/1997 | Poore |
| 5,704,345 A | 1/1998 | Berthon-Jones |
| 5,704,366 A | 1/1998 | Tacklind et al. |
| 5,711,297 A | 1/1998 | Iliff |
| 5,713,350 A | 2/1998 | Yokota et al. |
| 5,720,770 A | 2/1998 | Nappholz et al. |
| 5,720,771 A | 2/1998 | Snell |
| 5,724,580 A | 3/1998 | Levin et al. |
| 5,724,983 A | 3/1998 | Selker et al. |
| 5,738,102 A | 4/1998 | Lemelson |
| 5,743,267 A | 4/1998 | Nikolic |
| 5,749,907 A | 5/1998 | Mann |
| 5,749,908 A | 5/1998 | Snell |
| 5,752,976 A | 5/1998 | Duffin et al. |
| 5,769,074 A | 6/1998 | Barnhill et al. |
| 5,772,586 A | 6/1998 | Heinonen et al. |
| 5,772,599 A | 6/1998 | Nevo et al. |
| 5,772,604 A | 6/1998 | Langberg et al. |
| 5,778,882 A | 7/1998 | Raymond et al. |
| 5,785,650 A | 7/1998 | Akasaka et al. |
| 5,785,660 A | 7/1998 | Van Lake et al. |
| 5,788,640 A | 8/1998 | Peters |
| 5,788,643 A | 8/1998 | Feldman |
| 5,792,062 A | 8/1998 | Poon et al. |
| 5,819,251 A | 10/1998 | Kremer et al. |
| 5,855,593 A | 1/1999 | Olson et al. |
| 5,860,918 A | 1/1999 | Schradi et al. |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,911,132 A | 6/1999 | Sloane |
| 5,931,857 A | 8/1999 | Prieve et al. |
| 5,954,640 A | 9/1999 | Szabo |
| 5,957,861 A | 9/1999 | Combs et al. |
| 5,974,124 A | 10/1999 | Schlueter, Jr. et al. |
| 5,987,352 A | 11/1999 | Klein et al. |
| 5,993,386 A | 11/1999 | Ericsson |
| 6,004,276 A | 12/1999 | Wright et al. |
| 6,014,581 A | 1/2000 | Whayne et al. |
| 6,024,699 A | 2/2000 | Surwit et al. |
| 6,038,469 A | 3/2000 | Karlsson et al. |
| 6,047,203 A | 4/2000 | Sackner et al. |
| 6,050,940 A | 4/2000 | Braun |
| 6,063,028 A | 5/2000 | Luciano |
| 6,067,466 A | 5/2000 | Selker |
| 6,073,046 A | 6/2000 | Patel |
| 6,080,106 A | 6/2000 | Lloyd et al. |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,120,442 A * | 9/2000 | Hickey .......................... 600/300 |
| 6,122,351 A | 9/2000 | Schlueter, Jr. et al. |
| 6,129,675 A | 10/2000 | Jay |
| 6,132,384 A | 10/2000 | Christopherson et al. |
| 6,135,951 A | 10/2000 | Richardson et al. |
| 6,139,494 A | 10/2000 | Cairnes |
| 6,152,882 A | 11/2000 | Prutchi |
| 6,155,267 A | 12/2000 | Nelson |
| 6,168,563 B1 | 1/2001 | Brown |
| 6,168,653 B1 | 1/2001 | Myers |
| 6,171,237 B1 | 1/2001 | Avitall et al. |
| 6,171,256 B1 | 1/2001 | Joo et al. |
| 6,223,078 B1 | 4/2001 | Marcovecchio |
| 6,225,901 B1 | 5/2001 | Kail, IV |
| 6,234,964 B1 | 5/2001 | Iliff |
| 6,238,349 B1 | 5/2001 | Hickey |
| 6,246,992 B1 | 6/2001 | Brown |
| 6,249,705 B1 | 6/2001 | Snell |
| 6,250,309 B1 | 6/2001 | Krichen et al. |
| 6,263,245 B1 | 7/2001 | Snell |
| 6,283,923 B1 | 9/2001 | Finkelstein et al. |
| 6,287,252 B1 | 9/2001 | Lugo |
| 6,290,646 B1 | 9/2001 | Cosentino et al. |
| 6,302,844 B1 | 10/2001 | Walker et al. |
| 6,306,088 B1 | 10/2001 | Krausman et al. |
| 6,336,900 B1 | 1/2002 | Alleckson |
| 6,360,123 B1 | 3/2002 | Kimchi |
| 6,363,282 B1 | 3/2002 | Nichols et al. |
| 6,368,283 B1 * | 4/2002 | Xu et al. ....................... 600/485 |
| 6,416,471 B1 | 7/2002 | Kumar |
| 6,428,483 B1 | 8/2002 | Carlebach |
| 6,442,433 B1 | 8/2002 | Linberg |
| 6,454,705 B1 | 9/2002 | Cosentino |
| 6,463,326 B1 | 10/2002 | Hartley et al. |
| 6,477,424 B1 | 11/2002 | Thompson et al. |
| 6,512,949 B1 | 1/2003 | Combs et al. |
| 6,522,914 B1 | 2/2003 | Huvelle et al. |
| 6,584,353 B2 * | 6/2003 | Meyer ............................ 607/27 |
| 6,662,032 B1 | 12/2003 | Gavish et al. |
| 6,748,262 B2 | 6/2004 | Harada et al. |
| 6,827,670 B1 | 12/2004 | Stark et al. |
| 6,832,113 B2 | 12/2004 | Belalcazar |
| 7,366,569 B2 | 4/2008 | Belalcazar |
| 7,488,290 B1 | 2/2009 | Stahmann et al. |
| 7,621,879 B2 | 11/2009 | Eigler et al. |
| 7,711,415 B1 | 5/2010 | Farazi et al. |
| 7,794,404 B1 | 9/2010 | Gutfinger et al. |
| 2002/0123674 A1 | 9/2002 | Plicchi et al. |
| 2003/0055679 A1 | 3/2003 | Soll et al. |
| 2004/0019285 A1 | 1/2004 | Eigler et al. |
| 2005/0215914 A1 | 9/2005 | Bornzin et al. |
| 2006/0167363 A1 | 7/2006 | Osypka et al. |
| 2007/0161914 A1 | 7/2007 | Zdeblick et al. |
| 2010/0016731 A1 | 1/2010 | Eggers et al. |
| 2010/0016918 A1 | 1/2010 | Mann et al. |

FOREIGN PATENT DOCUMENTS

| | | |
|---|---|---|
| EP | 0 531 889 | 3/1993 |
| EP | 0 711 531 | 5/1996 |

(56) References Cited

FOREIGN PATENT DOCUMENTS

| WO | WO 97/39792 | 10/1997 |
|---|---|---|
| WO | WO 98/07142 | 2/1998 |
| WO | WO 98/42103 | 9/1998 |
| WO | WO 99/46718 | 9/1999 |
| WO | WO 99/55226 | 11/1999 |

OTHER PUBLICATIONS

Dunn et al., "Telemedicine Links Patients in Sioux Lookout with Doctors in Toronto," CMA Journal, vol. 122, pp. 484-487 (Feb. 23, 1980).

E. Braunwald, "Heart Disease—A Textbook of Cardiovascular Medicine," pp. 46-52 (5th Ed. 1997).

E. Hammond, "National Committee On Vital And Health Statistics, Subcommittee on Health Data Needs, Standards and Security," http://www.ncvhs.hhs.gov/970211t3.htm, pp. 1-4 (Feb. 11, 1997).

EP Search Report, Office Actions and Responses for co-pending EP Patent Application No. 00201939.6, filed May 31, 2000, entitled "System and Method for Automated Collection and Analysis of Regularly Retrieved Patient Information for Remote Patient Care" (48 pages).

File History (as of Aug. 12, 2011) for co-pending U.S. Appl. No. 11/367,852, filed Mar. 3, 2006 entitled "System and Method for Assessing Cardiac Performance Through Cardiac Vibration Monitoring" (278 pages).

File History (as of Sep. 15, 2010) for co-pending U.S. Appl. No. 10/782,642, filed Feb. 19, 2004 entitled "System and Method for Evaluating Cardiac Performance Relative to Performance of an Intrathoracic Pressure Maneuver" (229 pages).

File History (as of Jun. 17, 2011) for co-pending U.S. Appl. No. 12/349,413, filed Jan. 6, 2009 entitled "System and Method for Evaluating Cardiac Performance Relative to Performance of an Intrathoracic Pressure Maneuver" (190 pages).

Hamilton et al., "Arterial, Cerebrospinal and Venous Pressure in Man During Cough and Strain," 144 Am. J. of Phys., pp. 42, 42-50 (1944).

Health Insurance Portability And Accountability Act of 1996, Pub. L. No. 104-191, 110 Stat. 1936 (Aug. 21, 1996).

Hutten et al., "Cardiac Telemonitoring by Integrating Pacemaker Telemetry within Worldwide Data Communication Systems," Proceedings of 19th International Conference, IEEE/EMBS, Chicago, IL, pp. 974-976 (Oct. 30-Nov. 2, 1997).

Long WJ, et al., "Differential Diagnosis Generation From A Causal Network With Probabilities," Computers in Cardiology, 1988, Proceedings, pp. 185-188, Washington DC, USA.

Magrabi et al., "Web Based Longitudinal ECG Monitoring," Proceedings of 20th Annual International Conference of the IEEE Engineering in Medicine and Biology Society, vol. 20, No. 3, pp. 1155-1158 (1998).

McKay et al., "Instantaneous Measurement of Left and Right Ventricular Stroke Volume and Pressure-Volume Relationships with an Impedance Catheter," Circ. 69, No. 4, pp. 703-710 (1984).

Moody GB, "Integration of Real-Time and Off-Line Clinical Data in the MIMIC Database," Computers in Cardiology 1997 vol. 24, pp. 585-588, Cambridge, MA USA.

Nelwan et al., "Ubiquitous Access to Real-Time Patient Monitoring Data," Computers in Cardiollogy., vol. 24, pp. 271-274 (1997).

Roberge et al., "Basic and Applied Biomedical Engineering Building Blocks for Health Care," 1995 IEEE Engineering in Medicine and Biology 17th Annual Conference, vol. 1, Montreal-Canada, (Sep. 20-23, 1995).

Schreier et al., "A Non-Invasive Rejection Monitoring System Based on Remote Analysis of Intramyocardial Electrograms from Heart Transplants," IEEE, pp. 35-36 (1997).

Seborg et al., "Process Dynamics and Control," pp. 165-167, John Wiley & Sons (1989).

Security And Electronics Signature Standards; Proposed Rule, Federal Register, vol. 63, No. 155 (Aug. 12, 1998).

Vargas, Juan E., "Home-Based Monitoring of Cardiac Patients," Dept. of Electr. & Comput. Eng., South Carolina Univ., Columbia, SC, Information Technology Applications in Biomedicine, Proceedings., 1998 IEEE International Conference, pp. 133-136 (May 16-17, 1998).

Wortel et al., "Impedance Measurements in the Human Right Ventricle Using a New Pacing System," Pacing Clinical Electrophysiology, vol. 14(9), pp. 1336-1342 (Sep. 1991).

Zema et al., "Left Ventricular Dysfunction—Bedside Valsalva Maneuver," Br. Heart J., pp. 44:560-569 (1980).

File History (Jun. 17, 2001 thru May 2, 2013) for co-pending U.S. Appl. No. 12/349,413, filed Jan. 6, 2009 (54 pages).

Partial File History (May 3, 2013 thru Mar. 12, 2014) for co-owned U.S. Appl. No. 12/349,413, filed Jan. 6, 2009 (27 pages).

\* cited by examiner

186

225

240

340

SYSTEM AND METHOD FOR ASSESSING CARDIAC PERFORMANCE THROUGH CARDIAC VIBRATION MONITORING

CROSS-REFERENCE TO RELATED APPLICATION

This patent application is a divisional of U.S. patent application, Ser. No. 11/367,852, issued on Sep. 27, 2011 as U.S. Pat. No. 8,025,624, which is a continuation-in-part of U.S. patent application, Ser. No. 10/782,642, issued on Feb. 10, 2009 as U.S. Pat. No. 7,488,290, the disclosures of which are incorporated by reference, and the priority filing dates of which are claimed.

FIELD OF THE INVENTION

The present invention relates in general to cardiac performance assessment and, in particular, to a system and method for assessing cardiac performance through cardiac vibration monitoring.

BACKGROUND OF THE INVENTION

Heart disease refers to several classes of cardio and cardiovascular disorders and co-morbidities relating to the heart and blood vessels. Generally, heart disease is treatable through medication, lifestyle modification and surgical intervention, which involves repairing damaged organs and tissue. Surgical intervention can also involve implanting active monitoring or therapy delivery devices, such as pacemakers and defibrillators, and passive intervention means.

Heart disease can lead to heart failure, a potentially fatal condition in which the heart is unable to supply blood sufficient to meet the metabolic demands of a body. In a clinical setting, cardiac performance, including potential heart failure, can be detected by measuring changes in arterial blood pressure immediately before, during and immediately after the performance of intrathoracic pressure maneuvers, known as dynamic auscultation, which includes the Valsalva and Müller maneuvers, such as described in Braunwald, "Heart Disease—A Textbook of Cardiovascular Medicine," pp. 46-52 (5$^{th}$ ed. 1997), the disclosure of which is incorporated by reference.

In particular, potential heart failure can be effectively and safely detected by evaluating the profile of arterial blood pressure and other cardiac dimensional measures relative to performance of the Valsalva maneuver, which involves forced expiration against a closed glottis for about 10-30 seconds. In a healthy person with no prior history of cardiovascular disease or a patient suffering from a diseased but not failed heart, left ventricular ejection fraction (LVEF) and left ventricular end diastolic pressure (LVEDP) change dramatically coincidental to performance of the Valsalva maneuver, whereas LVEF and LVEDP change only slightly in a heart failure patient, as discussed in Hamilton et al., *Arterial, Cerebrospinal and Venous Pressure in Man During Cough and Strain*, 144 Am. J. of Phys., pp. 42, 42-50 (1944) and Zema et al., *Left Ventricular Dysfunction—Bedside Valsalva Maneuver*, Br. Heart J., pp. 44:560-569 (1980), the disclosures of which are incorporated by reference.

Circulatory effects and arterial blood pressure profile undergo four well-documented phases during performance of the Valsalva maneuver. During Phase I (initial strain), systemic arterial pressure increases approximately equal to the increase in intrathoracic pressure. During Phase II (strain duration and cessation of breathing), pulse pressure narrows and systemic systolic pressure decreases. During Phase III (strain discontinuation and resumption of normal breathing), systolic pressure drops rapidly. During Phase IV (recovery), diastolic and systolic pressures overshoot and return to pre-maneuver levels. The four phases form a characteristic signature and periodic analysis of arterial blood pressure profile or blood pressure, specifically LVEF and LVEDP, throughout each phase can be indicative of the patient's heart failure status.

Regularly obtaining and evaluating LVEF and LVEDP for chronic cardiac performance assessment, however, can be difficult. Acute direct measurements can be obtained through catheterization and electrodes. LVEF and LVEDP can be measured directly through a catheter distally placed into the left ventricle, but the procedure is invasive and creates unfavorable risks. Pulmonary artery wedge pressure (PAWP), measured through right heart catheterization, can be used as a surrogate measure for LVEDP, but the procedure is also invasive and risky. Moreover, catheterization is impractical in a non-clinical setting. Finally, chronically implanted cardiac pressure electrodes, while less risky, are generally inaccurate and unreliable. Consequently, indirect measurements approximating LVEF and LVEDP are preferable for chronic cardiac assessment.

For example, intracardiac impedance is readily measured through cardiac impedance plethysmography and can be used as an indirect measure of LVEF and LVEDP. Changes in intracardiac impedance correlate to cardiac dimensional changes, such as described in McKay et al., *Instantaneous Measurement of Left and Right Ventricular Stroke Volume and Pressure-Volume Relationships with an Impedance Catheter*, Circ. 69, No, 4, pp. 703-710 (1984), the disclosure of which is incorporated by reference. Similarly, cardiac vibrations, or heart sounds, can be measured through the use of an acoustic microphone or accelerometer. The energy of the first heart sound is proportionate to the rate of rise of left ventricular pressure, which is proportionate to cardiac preload. As a result, by measuring intracardiac impedance or cardiac vibrations, a profile of LVEDP and LVEF response during performance of the Valsalva maneuver can be obtained indirectly without resorting to invasive direct measurement techniques. Similarly, changes in cardiac filling can be determined from the third and fourth heart sounds. Known plethysmography techniques for indirectly measuring intracardiac impedance, however, adapt poorly to effective chronic long-term monitoring.

U.S. Pat. No. 4,548,211 to Marks discloses the use of external admittance impedance plethysmography to measure pulsatile volume and net inflow in a limb or body segment. External electrodes are placed on the skin and a voltage is applied and sensed for use in determining absolute physiologic values of peak-to-peak pulsatile volume and peat net inflow. While instrumental in non-invasively measuring peripheral blood flow dynamics, the Marks device fails to measure or monitor cardiac dimensional changes through intracardiac impedance.

U.S. Pat. No. 5,788,643 to Feldman discloses a process for monitoring patients with chronic congestive heart failure (CHF) by applying a high frequency current between electrodes placed on the limbs of a patient. Current, voltage and phase angle are measured to calculate resistance, reactance, impedance, total body water and extracellular water, which are compared to a baseline for identifying conditions relating to CHF. The Feldman process is limited to operating on external peripheral electrodes and fails to measure or monitor cardiac dimensional changes through intracardiac impedance.

U.S. Pat. Nos. 6,120,442 and 6,238,349 both to Hickey disclose an apparatus and method for non-invasively determining cardiac performance parameters, including systolic time intervals, contractility indices, pulse amplitude ratios while performing the Valsalva maneuver, cardiac output indices, and pulse wave velocity indices. A catheter is inserted into the esophagus and a balloon is pressurized at a distal end, positioned adjacent to the aortic arch to sense aortic pressure. The affects of aortic pressure on the balloon are utilized to determine the cardiac performance parameters. The Hickey devices, while capable of assessing cardiac performance, must be performed in a clinical setting and fails to measure or monitor cardiac dimensional changes through intracardiac impedance.

U.S. Pat. Nos. 3,776,221 and 5,291,895 both to McIntyre disclose a pressure-sensing device for providing a signal representative of systemic arterial blood pressure before and after performance of the Valsalva maneuver. Specifically, an electrode placed on the skin generates a blood pressure signal and measures changes in amplitude before and after the Valsalva maneuver is performed. The McIntyre devices are limited to operating with external skin electrodes and fail to measure or monitor cardiac dimensional changes through intracardiac impedance.

Therefore, there is a need for an approach to assessing cardiac performance by indirectly measuring arterial blood pressure profile through intracardiac impedance or heart sounds, that is, cardiac vibrations, recorded relative to performance of intrathoracic pressure maneuvers, such as the Valsalva maneuver. Preferably, such an approach would analyze an intrathoracic pressure maneuver signature in a non-clinical setting on a regular basis for use in automated heart disease patient management.

SUMMARY OF THE INVENTION

A system and method for generating a cardiac performance assessment based on intracardiac impedance and, in a further embodiment, cardiac vibrations, are described. Intracardiac impedance measures or cardiac vibration measures are collected during the induced performance of an intrathoracic pressure maneuver, such as the Valsalva maneuver, using an implantable cardiac device. The start of the intrathoracic pressure maneuver is either expressly marked by the patient or implicitly derived by the implantable cardiac device or by an intrathoracic pressure sensing device. The collected intracardiac impedance measures are periodically evaluated for determining arterial blood pressure profile. The intracardiac impedance measures are correlated to arterial blood pressure and assigned to the respective phases of the Valsalva maneuver, if applicable. In a further embodiment, the collected cardiac vibration measures are periodically evaluated to identify S1 heart sounds. The S1 heart sounds are correlated to arterial blood pressure and assigned to the respective phases of the Valsalva maneuver, if applicable. An arterial blood pressure profile trend determined for each of the phases is evaluated and the overall set of trends is compared to the signature characteristic of the intrathoracic pressure maneuver under consideration. A cardiac performance assessment is generated based on the closeness of match to the characteristic signature and a notification is generated if the cardiac performance assessment varies beyond a set of predefined thresholds. In a still further embodiment, the necessity of therapy changes is evaluated and, if necessary, initiated.

An embodiment provides a system and method for evaluating cardiac performance relative to performance of an intrathoracic pressure maneuver. Blood pressure is indirectly sensed by directly collecting intracardiac impedance measures through an implantable medical device. Cardiac functional changes to the blood pressure are evaluated in response to performance of an intrathoracic pressure maneuver.

A further embodiment provides a system and method for assessing cardiac performance through transcardiac impedance monitoring. Intracardiac impedance measures are directly collected through an implantable medical device. The intracardiac impedance measures are correlated to cardiac dimensional measures relative to performance of an intrathoracic pressure maneuver. The cardiac dimensional measures are grouped into at least one measures set corresponding to a temporal phase of the intrathoracic pressure maneuver. The at least one cardiac dimensional measures set is evaluated against a cardiac dimensional trend for the corresponding intrathoracic pressure maneuver temporal phase to represent cardiac performance.

A still further embodiment provides a system and method for evaluating cardiac performance relative to performance of an intrathoracic pressure maneuver. Heart sounds are indirectly sensed by directly collecting cardiac vibration measures through an implantable medical device. Cardiac functional changes to the heart sounds are evaluated in response to performance of an intrathoracic pressure maneuver.

A still further embodiment provides a system and method for assessing cardiac performance through cardiac vibration monitoring. Cardiac vibration measures are directly collected through an implantable medical device. Cardiac events including at least one first heart sound reflected by the cardiac vibration measures are identified. The first heart sound is correlated to cardiac dimensional measures relative to performance of an intrathoracic pressure maneuver. The cardiac dimensional measures are grouped into at least one measures set corresponding to a temporal phase of the intrathoracic pressure maneuver. The at least one cardiac dimensional measures set is evaluated against a cardiac dimensional trend for the corresponding intrathoracic pressure maneuver temporal phase to represent cardiac performance Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Internal Transcardiac Impedance Monitoring System

Figure 1:
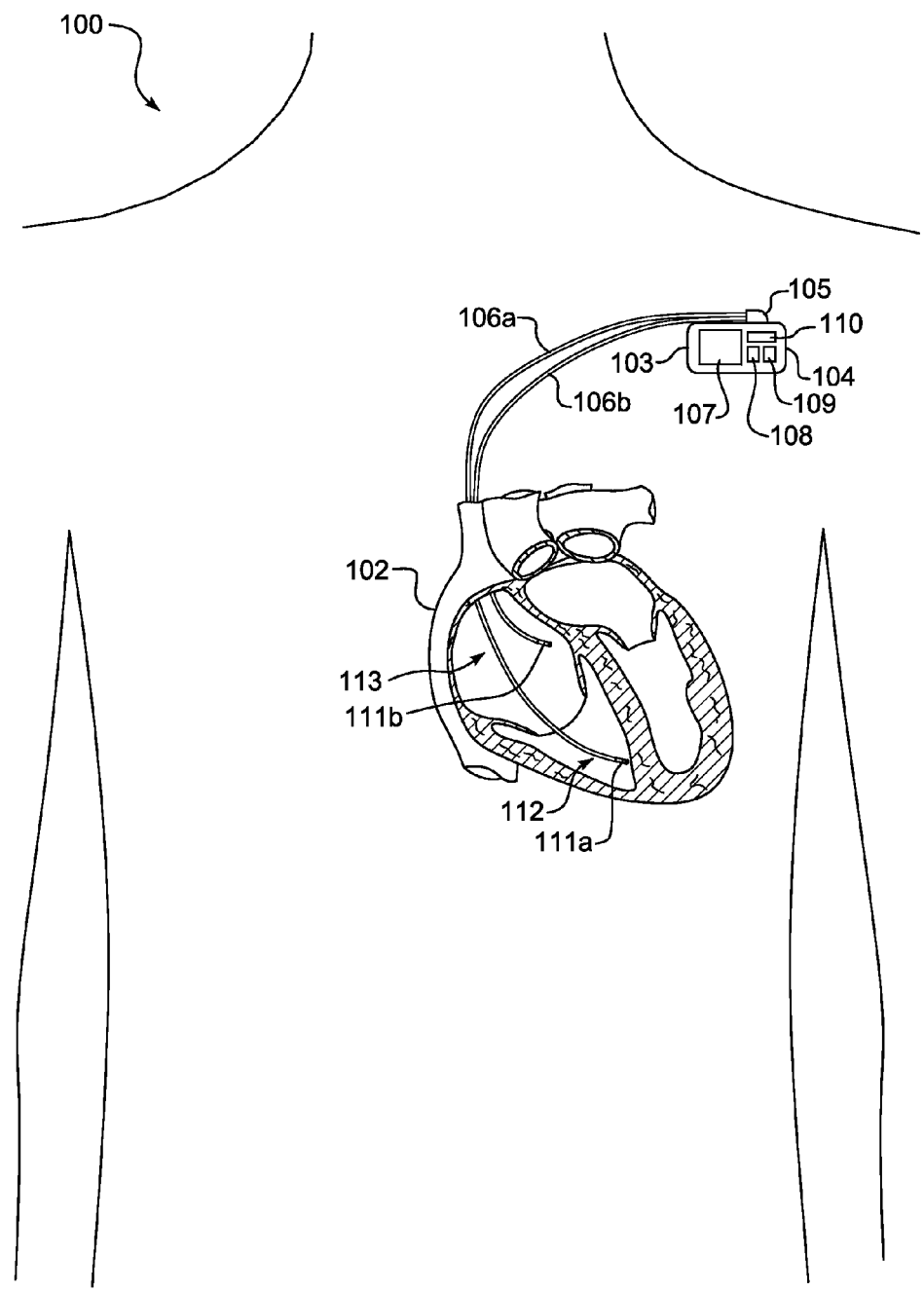
FIG. 1 is a schematic diagram showing an implantable medical device monitoring transcardiac impedance, in accordance with a further embodiment of the present invention.

FIG. 1 is a schematic diagram 100 showing an implantable medical device (IMD) 103 monitoring transcardiac impedance, in accordance with a further embodiment of the present invention. The IMD 103 is surgically implanted in the chest or abdomen of a patient and consists generally of a housing 104 and terminal block 105. The IMD 103 is coupled to a set of leads 106a-b at the terminal block 105. During surgery, the leads 106a-b are threaded through a vein and placed into the heart 102 with the distal tips of each lead 106a-b positioned in direct contact with tissue inside the heart 102.

The housing 104 contains a battery 107, control circuitry 108, memory 109, and telemetry circuitry 110. The battery 107 provides a finite power source for the IMD components. The control circuitry 108 samples and processes raw data signals and includes signal filters and amplifiers, memory and a microprocessor-based controller, as would be appreciated by one skilled in the art. In a further embodiment, the control circuitry 108 includes an accelerometer for sensing energies associated with mechanical vibrations of the heart, including audible and inaudible energies. In a still further embodiment, the control circuitry 108 receives an acoustic signal indicative of one or more types of heart sounds acquired by a microphone sensing acoustic energies generated by the mechanical vibrations of the heart. As used herein, the term "heart sounds" refers to cardiac vibrations and includes auscultatory, sub-audible, and various forms of detectable cardiac events. The acoustic signal can be rectified and passed through a low-pass or band-pass filter. The memory 109 includes a short-term, volatile memory store in which raw physiological signals can be stored as telemetered signals for later retrieval and analysis. The telemetry circuitry 110 provides an interface between the IMD 103 and external devices (not shown). The telemetry circuitry 110 enables operating parameters to be non-invasively programmed into the memory 109 through an external device in telemetric communication with the IMD 103. The telemetry circuitry 110 also allows patient information collected by the IMD 103 and transiently stored in the memory 109 to be sent to the external device for processing and analysis.

The IMD 103 is in direct electrical communication with the heart 102 through electrodes 111a-b positioned on the distal tips of each lead 106a-b. By way of example, the set of leads 106a-b can include a right ventricular electrode 111a and a right atrial electrode 111b. The right ventricular electrode 111a is preferably placed in the right ventricular apex 112 of the heart 102 and the right atrial electrode 111b is preferably placed in the right atrial chamber 113 of the heart 102. The electrodes 111a-b enable the IMD 103 to directly collect raw physiological measures, preferably through millivolt measurements. Other configurations and arrangements of leads and electrodes, including the use of single and multiple leads arrays and single and multiple electrodes, can be used, as would be recognized by one skilled in the art.

In the described embodiment, the IMD 103 can be implemented as part of cardiac pacemakers used for managing bradycardia, implantable cardioverter defibrillators (IMDs) used for treating tachycardia, and other types of implantable cardiovascular monitors and therapeutic devices used for monitoring and treating heart failure, structural problems of the heart, such as congestive heart failure, rhythm problems, and other heart conditions, as would be appreciated by one skilled in the art. Examples of cardiac pacemakers suitable for use in the described embodiment include the Pulsar Max II, Discovery, and Discovery II pacing systems, sold by Guidant Corporation, St. Paul, Minn. An example of an IMD suitable for use in the described embodiment includes the Contak Renewal cardiac resynchronization therapy defibrillator, also sold by Guidant Corporation, St. Paul, Minn.

On a regular basis, the telemetered signals stored in the memory 109 are retrieved. By way of example, a programmer (not shown) can be used to retrieve the telemetered signals. However, any form of programmer, interrogator, recorder, monitor, or telemetered signals transceiver suitable for communicating with IMD 103 could be used, including a dedicated patient management device, as further described below with reference to FIG. 3. In addition, a server, personal computer or digital data processor could be interfaced to the IMD 103, either directly or via a telemetered signals transceiver configured to communicate with the implantable medical device 103.

The programmer communicates with the IMD 103 via radio frequency signals exchanged through a wand placed over the location of the IMD 103. Programming or interrogating instructions are sent to the IMD 103 and the stored telemetered signals are downloaded into the programmer. Once downloaded, the telemetered signals can be sent via a network, such as the Internet, to a server (not shown), which periodically receives and stores the telemetered signals in a database, as further described below with reference to FIG. 7.

An example of a programmer suitable for use in the present invention is the Model 2901 Programmer Recorder Monitor, manufactured by Guidant Corporation, Indianapolis, Ind., which includes the capability to store retrieved telemetered signals on a proprietary removable floppy diskette. The telemetered signals could later be electronically transferred using a personal computer or similar processing device, as would be appreciated by one skilled in the art.

Other alternate telemetered signals transfer means could also be employed. For instance, the stored telemetered signals could be retrieved from the IMD 103 and electronically transferred to a network using a combination of a remote external programmer and analyzer and a remote telephonic communicator, such as described in U.S. Pat. No. 5,113,869, the disclosure of which is incorporated by reference. Similarly, the stored telemetered signals could be retrieved and remotely downloaded to a server using a world-wide patient location and data telemetry system, such as described in U.S. Pat. No. 5,752,976, the disclosure of which is incorporated herein by reference.

Externally-Assisted Transcardiac Impedance Monitoring System

Figure 2:
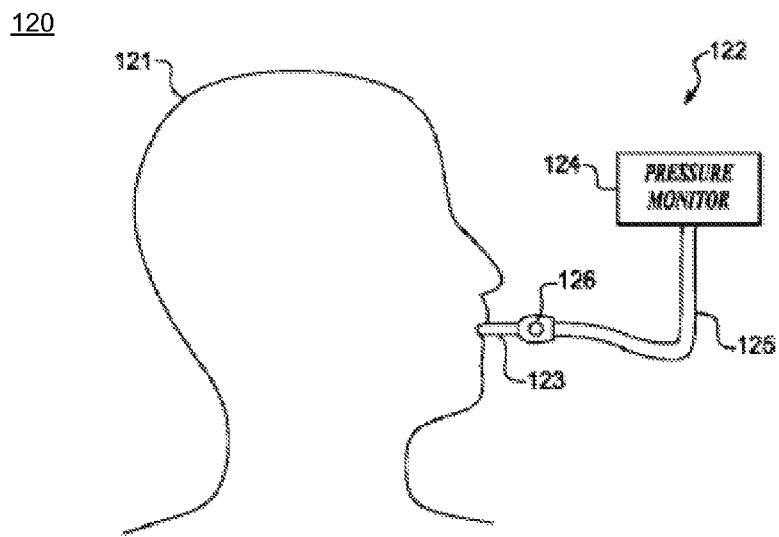
FIG. 2 is a schematic diagram showing an external medical device assisting in monitoring transcardiac impedance, in accordance with a further embodiment of the present invention.

FIG. 2 is a schematic diagram 120 showing an external medical device 122 assisting in monitoring transcardiac impedance, in accordance with a further embodiment of the present invention. The external medical device 122 facilitates transcardiac impedance monitoring by ensuring consistent intrathoracic pressure, particularly when thoracic pressure is elevated when induced, for instance, by performance of the Valsalva maneuver. In a further embodiment, the external medical device 122 facilitates cardiac vibration monitoring to identify cardiac events, such as auscultatory, sub-audible, and various forms of detectable cardiac events. The external medical device 122 includes a mouthpiece 123 functionally connected to a pressure monitor 124 via a hose 125. The pressure monitor 124 defines a confined volume into which the patient 121 blows. A pressure regulating device 126 releases expired air. The pressure monitor 124 provides a pressure reading representative of the pressure in the confined volume. The pressure monitor 124 can also provide recording functions that record the pressure levels during performance of a transcardiac maneuver by a patient 121.

In a further embodiment, a thoracic pressure electrode, such as described in U.S. Pat. No. 6,132,384, the disclosure of which is incorporated by reference, can be combined with the IMD 103 to provide a fully implanted solution. The use of an implanted thoracic pressure electrode enables measurements during normal activities of daily living that produce elevated thoracic pressure similar to an induced performance of the Valsalva maneuver. When an elevated thoracic pressure is detected by the implanted thoracic pressure electrode, intracardiac impedance is recorded by the IMD 103 on a continuous basis. After the cardiac response period ends, the recorded intracardiac impedance data can either be downloaded to an external device (not shown) for further analysis, as further described below with reference to FIG. 12, or can be analyzed by the IMD 103.

Automated Patient Management Environment

Figure 3:
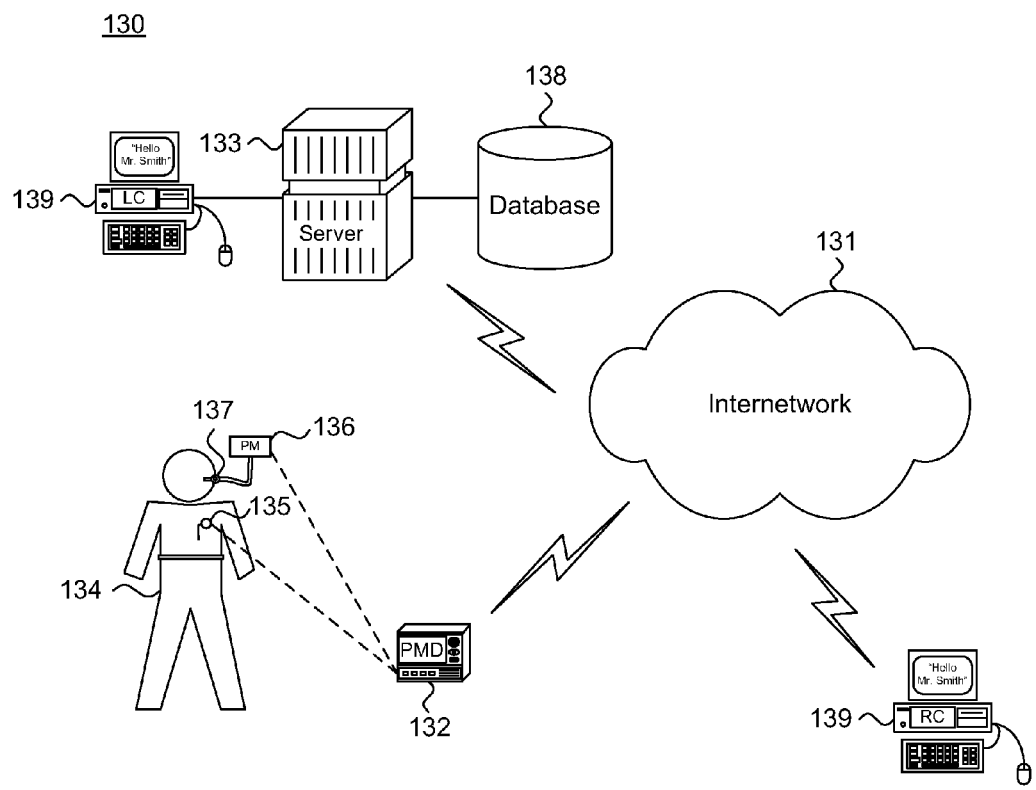
FIG. 3 is a functional block diagram showing, by way of example, an automated patient management environment.

Cardiac performance can be assessed remotely through automated patient management. Automated patient management encompasses a range of activities, including remote patient management and automatic diagnosis of patient health, such as described in commonly-assigned U.S. Patent application Pub. No. US2004/0103001, published May 27, 2004, pending, the disclosure of which is incorporated by reference. Such activities can be performed proximal to a patient, such as in the patient's home or office, centrally through a centralized server, such from a hospital, clinic or physician's office, or through a remote workstation, such as a secure wireless mobile computing device. FIG. 3 is a functional block diagram showing, by way of example, an automated patient management environment 130. In one embodiment, a patient 134 is proximal to one or more patient monitoring or communications devices, such as a patient management device 132, which are interconnected remotely to a centralized server 133 over an internetwork 131, such as the Internet, or through a public telephone exchange (not shown), such as a conventional or mobile telephone network. Other patient monitoring or communications devices are possible. In addition, the functionality provided by the centralized server 133 could also be provided by local or decentralized servers, or by workstations, personal computers, or other computational systems accessible via the internetwork 131 or other form of network. The internetwork 131 can provide both conventional wired and wireless interconnectivity. In one embodiment, the internetwork 131 is based on the Transmission Control Protocol/Internet Protocol (TCP/IP) network communication specification, although other types or combination of networking implementations are possible. Similarly, other network topologies and arrangements are possible.

Each patient management device 132 is uniquely assigned to a patient under treatment 134 to provide a localized and network-accessible interface to one or more medical devices, such as an IMD 135, either through direct means, such as wired connectivity, where applicable, or through indirect means, such as selective radio frequency or wireless telemetry based on, for example, "strong" Bluetooth or IEEE 802.11 wireless fidelity "WiFi" and "WiMax" interfacing standards. Other configurations and combinations of patient data source interfacing are possible. Medical therapy devices include implantable medical devices (IMDs) 135, such as pacemakers, implantable cardiac defibrillators (ICDs), drug pumps, and neuro-stimulators, as well as external medical devices (not shown). Medical sensors include implantable sensors (not shown), such as implantable heart and respiratory monitors and implantable diagnostic multi-sensor non-therapeutic devices, and external sensors (not shown), such as Holter monitors, weight scales, and blood pressure cuffs. Other types of medical therapy, medical sensing, and measuring devices, both implantable and external, are possible.

Patient data includes physiological measures, which can be quantitative or qualitative, including cardiac vibrations measures, parametric data regarding the status and operational characteristics of the patient data source itself, and environmental parameters, such as the temperature or time of day. In a further embodiment, patient data can also include psychological, drug dosing, medical therapy, and insurance-related information, as well as other types and forms of information, such as digital imagery or sound and patient-provided or -uploaded information. The medical devices collect and forward the patient data either as a primary or supplemental function. Other types of patient data are possible. Each medical device can generate one or more types of patient data and can incorporate one or more components for delivering therapy, sensing physiological data, measuring environmental parameters, or a combination of functionality.

Periodically, or on demand, the server 133 receives patient data 206 from each patient monitoring or communications device, which is processed to identify cardiac vibrations, including auscultatory sub-audible, and various forms of detectable cardiac events, including one or more heart sounds, and to assess cardiac performance, as further described below beginning with reference to FIG. 16. The patient data, which includes raw physiological measures and other data, is processed and stored into a database 138, which can also include a patient history generated on a monthly, quarterly, or other periodic basis, that can be referenced to detect heart failure progression and, if appropriate, initiate specific therapeutic changes. In a further embodiment, a pressure monitor 136, which includes a coupled mouth piece 137, interfaces to the patient management device 132 to supplement pressure measurement readings collected relative to performance of an intrathoracic pressure maneuver, such as the Valsalva or Müller maneuvers, as further described below beginning with reference to FIGS. 4A-C. Other intrathoracic pressure maneuvers are possible. Additionally, other types of patient data collection, periodicity and storage are possible.

In a further embodiment, the collected patient data can also be accessed and analyzed by one or more clients 139, either locally-configured or remotely-interconnected over the internetwork 131. The clients 139 can be used, for example, by clinicians to securely access stored patient data assembled in the database 138 and to select and prioritize patients for health care provisioning, such as respectively described in commonly-assigned U.S. patent application Ser. No. 11/121,593, filed May 3, 2005, pending, and U.S. patent application Ser. No. 11/121,594, filed May 3, 2005, pending, the disclosures of which are incorporated by reference. Although described herein with reference to physicians or clinicians, the entire discussion applies equally to organizations, including hospitals, clinics, and laboratories, and other individuals or interests, such as researchers, scientists, universities, and governmental agencies, seeking access to the patient data.

In a further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Preferably, the server 133 is a computing platform configured as a uni-, multi- or distributed processing system, and the clients 139 are general-purpose computing workstations, such as a personal desktop or notebook computer. In addition, the patient management device 132, server 133 and clients 139 are programmable computing devices that respectively execute software programs and include components conventionally found in computing device, such as, for example, a central processing unit (CPU), memory, network interface, persistent storage, and various components for interconnecting these components.

Arterial Blood Pressure Profiles

Figure 4A:
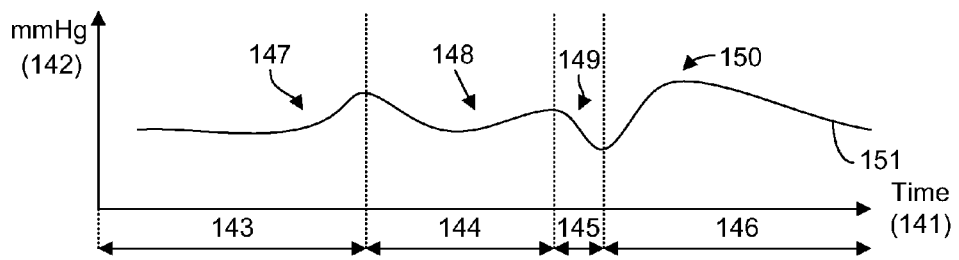
FIGS. 4A-C are graphical representations showing, by way of example, averaged arterial blood pressure profiles relative to performance of the Valsalva maneuver in a healthy person, a patient suffering from heart disease and a patient suffering from heart failure.
Figure 4B:
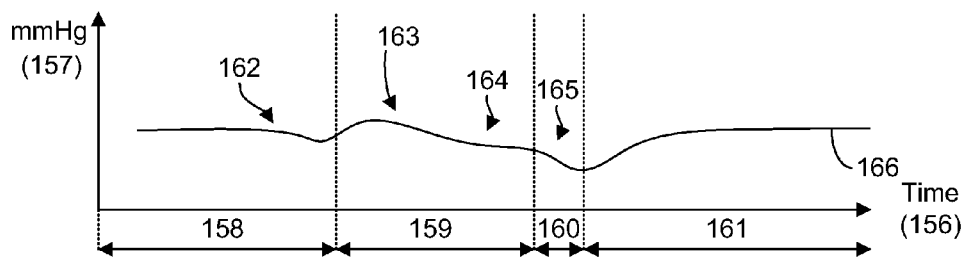
Figure 4C:
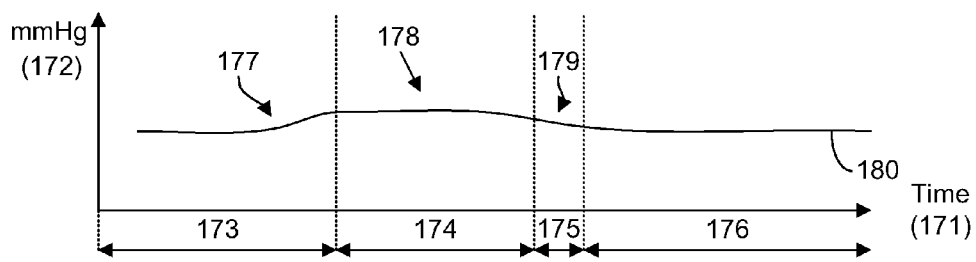

FIGS. 4A-C are graphical representations showing, by way of example, averaged arterial blood pressure profiles 140, 155, 170 relative to performance of the Valsalva maneuver in a healthy person, a patient suffering from heart disease but not significant heart failure and a patient suffering from significant heart failure, respectively. The x-axis 141, 156, 171 respectively represent time. The y-axis 142, 157, 172 respectively indicate arterial pressure (mmHg). Averaged changes in arterial pressure are plotted over time throughout each of the four phases 143-146, 158-161, 173-176 of the Valsalva maneuver, respectively. For clarity, the pulsatile arterial blood pressure changes are shown as averaged values and each of the averaged arterial blood pressure profiles 140, 155, 170 have respectively been normalized relative to time.

The Valsalva maneuver involves deep inspiration followed by forced exhalation against a closed glottis for ten to twelve seconds. The four phases of the Valsalva maneuver exhibit characteristic signatures for normal healthy people and for patients suffering from heart disease, but not significant heart failure, and for patients suffering from significant heart failure. During Phase I, initial strain, systemic blood pressure undergoes a transient rise as straining commences. During Phase II, strain duration and cessation of breathing, systemic venous return, blood pressure and pulse pressure decrease perceptibly. During Phase III, strain discontinuation and resumption of normal breathing, blood pressure and systemic venous return exhibit abrupt, transient decreases. During Phase IV, recovery, systemic arterial pressure overshoots with reflex bradycardia. However, for patients suffering from heart failure, the response signature is a muted square wave response with a slight elevation in blood pressure during Phase III and minimal perceptible changes during Phases I, II and IV.

Cardiac performance response profile is significantly dependent on left ventricular function, specifically LVEF and mean LVEDP. A healthy person with no history of cardiovascular diseases may, for example, be expected to have an LVEF and mean LVEDP of approximately 70% and 14 mmHg, respectively. A patient suffering from heart disease but not significant heart failure may, for example, typically be expected to have an LVEF and mean LVEDP of approximately 50% and 20 mmHg, respectively. A patient suffering from heart failure may, for example, typically be expected to have an LVEF and mean LVEDP of approximately 30% and 40 mmHg, respectively.

Healthy Person

Referring first to FIG. 4A, the graphical representation shows, by way of example, an averaged arterial blood pressure profile 140 relative to performance of the Valsalva maneuver in a healthy person with no history of cardiovascular diseases. During Phase I 143, intrathoracic pressure increases in response to the strain associated with the maneuver, along with a sharp rise 147 in arterial pressure approximately equal to the intrathoracic pressure increase. During Phase II 144, pulse pressure narrows and arterial pressure undergoes a transient decrease 148. During Phase III 145, systolic pressure drops rapidly 149. Finally, during Phase IV 146, diastolic and systolic pressures return to pre-maneuver levels 151 following a large overshoot 150 in arterial pressure.

Patient Suffering from Heart Disease But Not Significant Heart Failure

Referring next to FIG. 4B, the graphical representation shows, by way of example, an averaged arterial blood pressure profile 155 relative to performance of the Valsalva maneuver in a patient suffering from heart disease but not significant heart failure. During Phase I 158, systemic arterial pressure increases only slightly 162. During Phase II 159, systemic arterial pressure 163 increases approximately equal to the increase in intrathoracic pressure followed by a narrowing of pulse pressure and arterial pressure decrease 164. During Phase III 160, systolic pressure drops rapidly 165. Finally, during Phase IV 161, diastolic and systolic pressures return to pre-maneuver levels 166 without overshoot.

Patient Suffering from Heart Failure

Finally, referring to FIG. 4C, the graphical representation shows, by way of example, an averaged arterial blood pressure profile 170 relative to performance of the Valsalva maneuver in a patient suffering from heart failure. During Phase I 173, almost no appreciable increase in systemic arterial pressure occurs 177. During Phase II 174, pulse pressure and systemic systolic pressure remain at approximately the same elevated level 178 throughout the phase. During Phase III 175, systolic pressure decreases to approximately the same level as in Phase I 173. During Phase IV 176, diastolic and systolic pressures return to their pre-maneuver levels 180 almost immediately upon cessation of strain.

Cardiac Dimension Profiles

Figure 5:
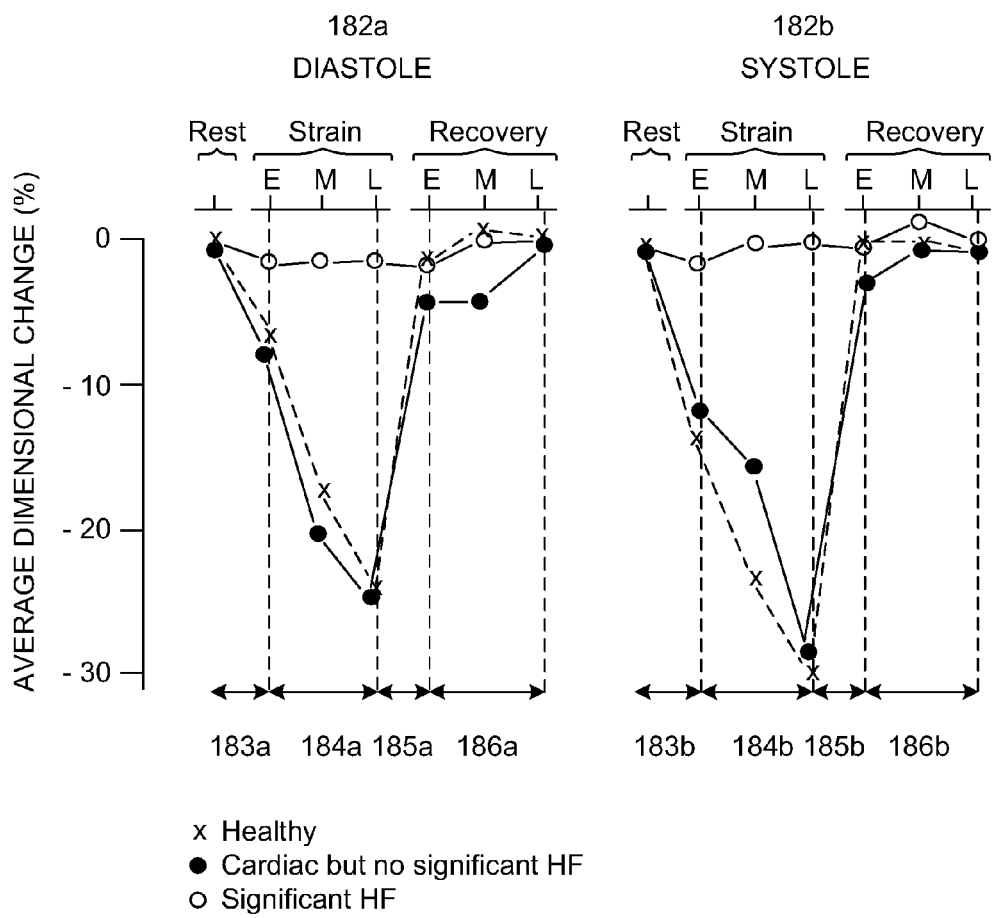
FIG. 5 is a graphical representation showing, by way of example, cardiac dimension profiles during diastole and systole, respectively, relative to performance of the Valsalva maneuver in a healthy person, a patient suffering from heart disease but not significant heart failure and a patient suffering from significant heart failure.

FIG. 5 is a graphical representation showing, by way of example, cardiac dimension profiles 182a, 182b, during diastole and systole, respectively, relative to performance of the Valsalva maneuver in a healthy person, a patient suffering from heart disease but not significant heart failure and a patient suffering from significant heart failure. The x-axis represents time. The y-axis indicates average dimensional change (%). Averaged changes in dimension are plotted over time throughout each of the four phases 183a-186a, 183b-186b of the Valsalva maneuver.

Healthy Person

During Phase I 183a, 183b, cardiac dimension decreases in response to the strain associated with the maneuver for a healthy person with no history of cardiovascular diseases. During Phase II 184a, 184b, cardiac dimension reduces rapidly. During Phase III 185a, 185b, cardiac dimension increases rapidly. Finally, during Phase IV 186a, 186b, cardiac dimension pressures return to pre-maneuver levels.

Patient Suffering from Heart Disease But Not Significant Heart Failure

The average cardiac dimensional change for a patient suffering from heart disease but not significant heart failure is essentially the same as the changes observed for a healthy person with no history of cardiovascular diseases.

Patient Suffering from Heart Failure

The average cardiac dimensional change for a patient suffering from significant heart failure reflects only slight changes during each of the four phases of a Valsalva maneuver.

Stroke Volume and Left Ventricular Pressure Profiles

Figure 6:
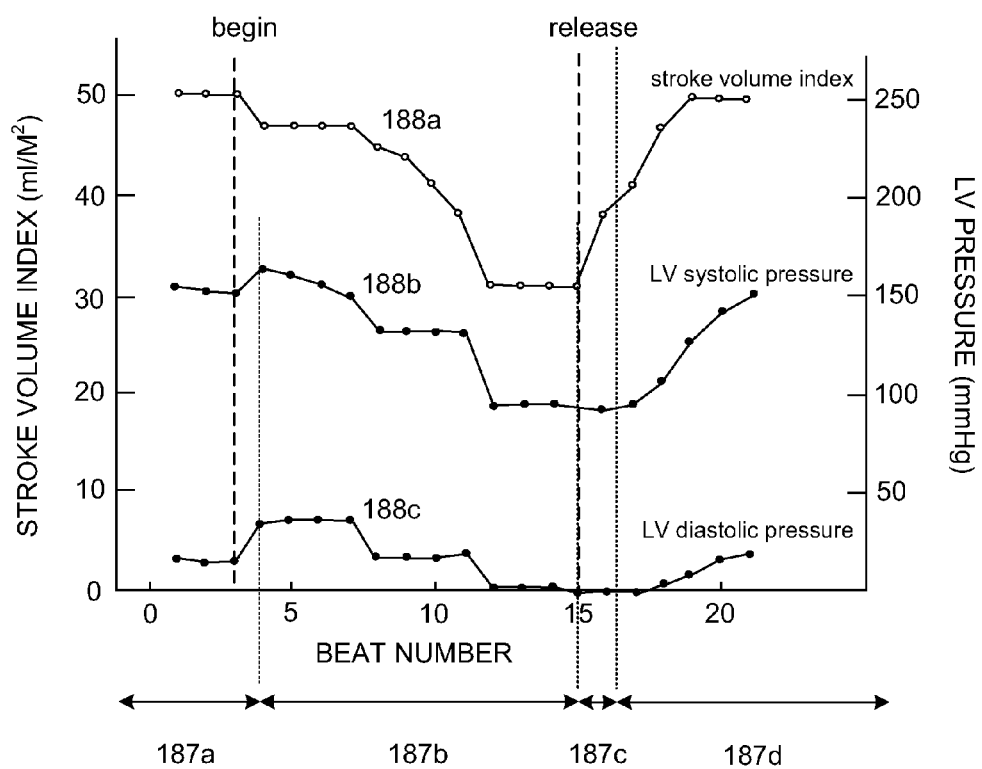
FIG. 6 is a graphical representations showing, by way of example, stroke volume index profile and left ventricular pressure profile relative to performance of the Valsalva maneuver in a healthy person.

FIG. 6 is a graphical representations showing, by way of example, stroke volume index profile 188a and left ventricular pressure profile 188b relative to performance of the Valsalva maneuver in a healthy person. The x-axis represents time. The left hand y-axis indicates stroke volume index (ml/M$^2$) and the right handy-axis indicates LV pressure. Changes in stroke volume index and left ventricular pressure are plotted over time throughout each of the four phases 187a, 187b, 187c and 187d of a Valsalva maneuver. During Phase I 187a, the stroke volume index decreases slightly and left ventricular systolic and diastolic pressures increase slightly. During Phase II 187b, the stroke volume index and left ventricular and diastolic systolic pressures decrease significantly. During Phase III 187c, the stroke volume index begins an increase towards pre-maneuver levels, but the left ventricular diastolic and systolic pressures remain stable. Finally, during Phase IV 187d, the stroke volume index and left ventricular diastolic and systolic pressures return to pre-maneuver levels.

LVEF and LVEDP Correlations

Heart disease patient management requires carefully monitoring and evaluation of LVEF and LVEDP. In heart failure patients, an increase in LVEDP can lead to an acute exasperation of heart failure and acute decompensation. Changes to LVEDP associated with the acute exasperation of heart failure can occur in a few days, whereas changes to LVEF occur more slowly and are associated with long-term changes. Thus, effectively assessing cardiac performance, particularly for heart disease and heart failure patients, requires evaluating LVEF and LVEDP or equivalent values that approximate LVEF and LVEDP changes, such as intracardiac impedance.

Comparing the averaged cardiac dimension profiles 182a, 182b described above with reference to FIG. 5, healthy people and patients suffering from heart disease undergo significant cardiac dimensional changes during performance of the Valsalva maneuver, while the cardiac dimensions in patients with significant heart failure change only slightly. Intracardiac impedance has been empirically correlated to changes in left ventricular pressure, such as described in Wortel et al., *Impedance Measurements in the Human Right Ventricular Using a New Pacing System*, Pacing Clinical Electrophysiology, Vol. 14(9), pp. 1336-42 (September 1991), the disclosure of which is incorporated by reference, and can therefore be used as a surrogate measure of cardiac dimensional changes.

In a further embodiment, the Müller maneuver is performed either in lieu of or in addition to the Valsalva maneuver. The Müller maneuver involves deep inspiration while the nose is held closed and mouth firmly sealed for ten seconds. The Müller maneuver exaggerates inspiration effort and augments murmurs and right side cardiac filling sounds.

System Modules

Figure 7:
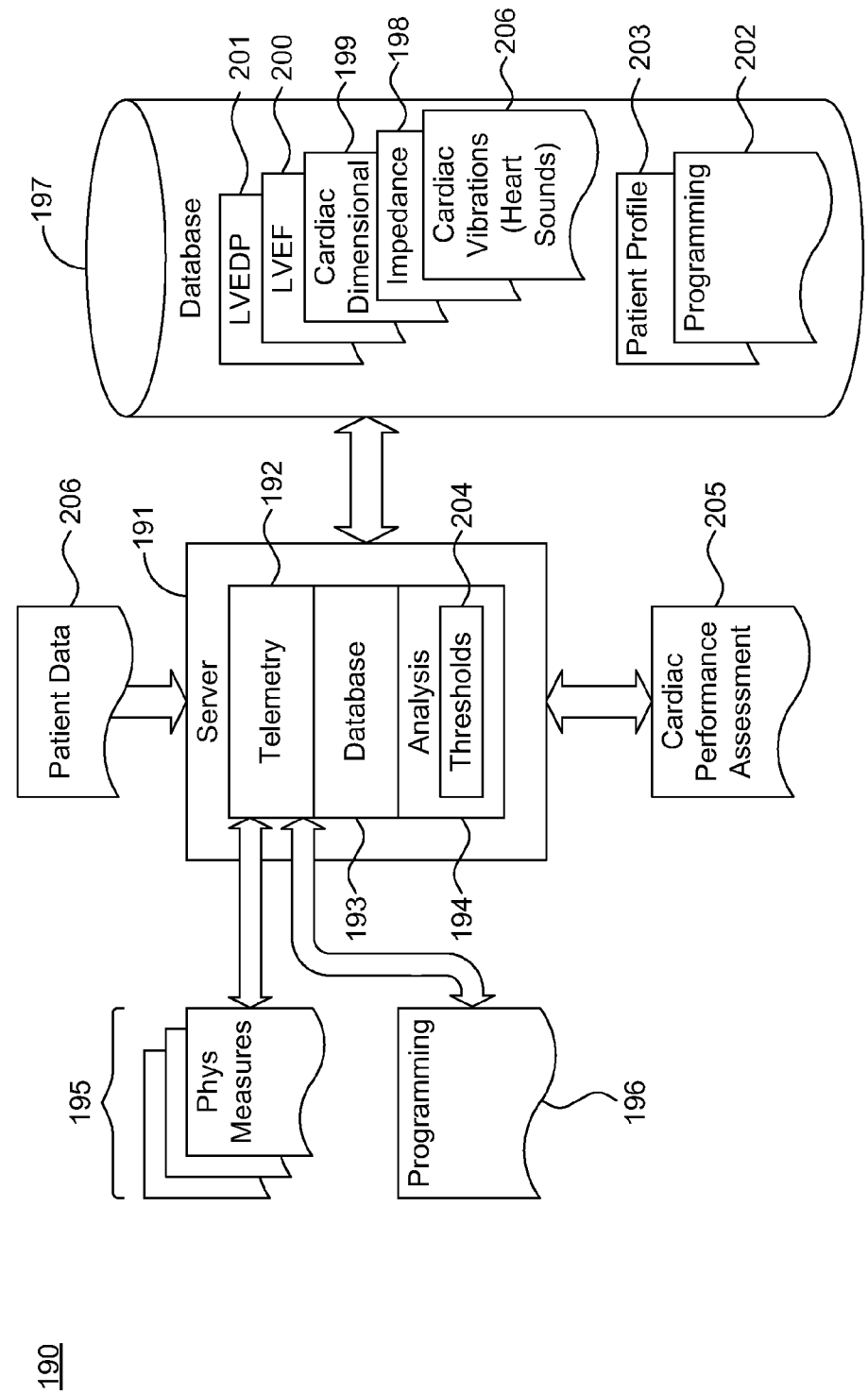
FIG. 7 is a functional block diagram showing a system for assessing cardiac performance through transcardiac impedance monitoring, in accordance with a further embodiment of the present invention.

FIG. 7 is a functional block diagram showing a system 190 for assessing cardiac performance through transcardiac impedance monitoring, in accordance with a further embodiment of the present invention. Each component is a computer program, procedure or process written as source code in a conventional programming language, such as the C++ programming language, and is presented for execution by one or more CPUs as object or byte code in a uniprocessing, distributed or parallelized configuration, as would be appreciated by one skilled in the art. The various implementations of the source code and object and byte codes can be held on a computer-readable storage medium or embodied on a transmission medium in a carrier wave.

The system 190 consists of a server 191 coupled to a database 197, which provides persistent secondary storage. The server 191 consists of three modules: telemetry 192, database 193, and analysis 194. The telemetry module 192 communicatively interfaces to the IMD 103 through a logically-formed, non-invasive communication channel, such as provided though induction, static magnetic field coupling, or by related means, as would be appreciated by one skilled in the art. The telemetry module 192 facilitates the transferal and exchange of physiological measures 195 and programming parameters 196 between the IMD 103 and the server 191. The physiological measures 195 include raw physiological data regularly collected by the IMD 103 and stored in the memory 109. The programming parameters 196 include monitoring and therapy delivery device configuration settings, which are exchanged between the IMD 103 and the server 191. The telemetry module 192 communicates with the telemetry circuitry 110 on the IMD 103 using standard programmer communication protocols, as would be appreciated by one skilled in the art.

For an exemplary cardiac implantable medical device, the physiological measures 195 and programming parameters 196 non-exclusively present patient information recorded on a per heartbeat, binned average or derived basis and relating to atrial electrical activity, ventricular electrical activity, minute ventilation, patient activity score, cardiac output score, mixed venous oxygenation score, cardiovascular pressure measures, time of day, the number and types of interventions made, and the relative success of any interventions, plus the status of the batteries and programmed settings.

The database module 193 maintains information stored in the database 197 as structured records for facilitating efficient storage and retrieval. The database module 193 stores the physiological measures 195 and programming parameters 196 exchanged with the IMD 103 in the database 197. The database 197 stores the physiological measures 195 as derived measures, which include, non-exclusively, impedance measures 198, cardiac dimensional measures 199, LVEF measures 200, and LVEDP measures 201. In a further embodiment, the database 197 further stores heart sounds 206, which are collected as cardiac vibration measures through the IMD 103. Other raw and derived measures can be stored in the database 197, as would be recognized by one skilled in the art. The programming parameters 196 are maintained in the database as programming values 202. In addition, patient profile information 203 is maintained in the database 197.

The analysis module 194 derives and evaluates the physiological data maintained in the database 197. As necessary, the physiological measures 195 retrieved from the IMD 103 are converted and derived into the impedance measures 198, cardiac dimensional measures 199, LVEF measures 200, and LVEDP 201, as would be appreciated by one skilled in the art. In particular, the impedance measures 198 are analyzed and evaluated to determine an overall arterial blood pressure profile, which is compared to predefined thresholds 204 for assessing cardiac performance relative to the performance of an intrathoracic pressure maneuver, as further described below with reference to FIG. 12. The analysis module 194 generates a cardiac performance assessment 205, which identifies trends indicating cardiovascular disease and, in particular, heart failure, absence, onset, progression, regression, and status quo. The cardiac performance assessment 205 can be further evaluated to determine whether medical intervention is necessary.

In a further embodiment, the analysis module 194 derives heart sounds 206 from the physiological measures 195. Cardiac vibrations, including auscultatory, sub-audible, and various forms of detectable cardiac events evaluated to identify S1 heart sounds and are processed to derive cardiac chamber pressures, including LVEF, LVEDP, pulmonary capillary wedge pressure, pulmonary artery pressure, and an S3 index of pressure, as further described below with reference to FIG. 18. The cardiac chamber pressures represent an overall arterial blood pressure profile, which is compared to the predefined thresholds 204 for assessing cardiac performance relative to the performance of an intrathoracic pressure maneuver.

In a still further embodiment, the functions of the server 191 are performed by the IMD 103 or PMD 132, which directly generates the cardiac performance assessment 205, for retrieval by an external device.

Arterial Blood Pressure Profile Trend Analysis

Figure 8:
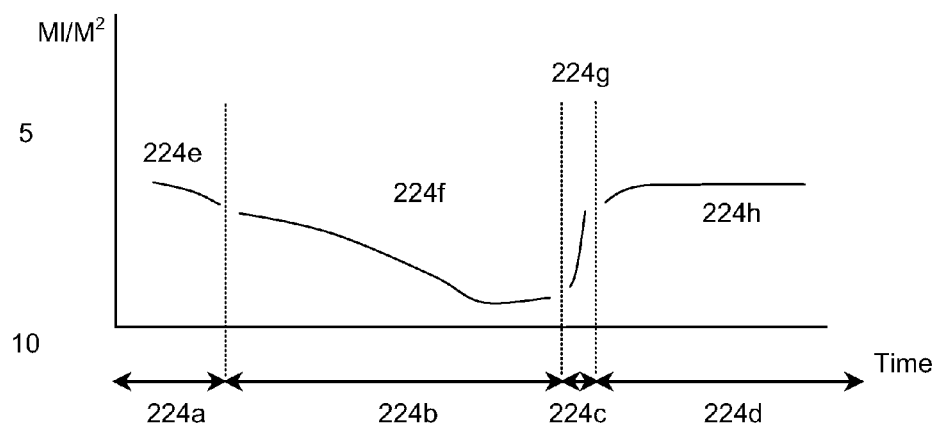
FIG. 8 is a graphical representation showing, by way of example, trend analysis of arterial blood pressure profile.

FIG. 8 is a graphical representation showing, by way of example, trend analysis 210 of arterial blood pressure profile 213. The x-axis 211 represents time. The y-axis 212 indicates arterial pressure in mmHg. Averaged changes in arterial pressure are plotted over time throughout each of the four phases 214-217 of the Valsalva maneuver.

The arterial blood pressure profile 213 models the characteristic signature exhibited during each phase of the Valsalva maneuver. During Phase I 214, the arterial pressure is evaluated for an increasing trend 218. During Phase II 215, the arterial pressure is evaluated for a transient decreasing trend 219. During Phase III 216, the arterial pressure is evaluated for a significantly decreasing trend 220. Finally, during Phase VI 217, the arterial pressure is evaluated for a steeply increasing trend 221, followed by an overshooting trend 222, followed by a decreasing trend 223 with resumption of normal arterial pressure. In addition to the arterial pressure trends 218-223, pulsatile volume and heart rate can also be evaluated for trends, as would be recognized by one skilled in the art.

Cardiac Stroke Volume Profile Trend Analysis

Figure 9:
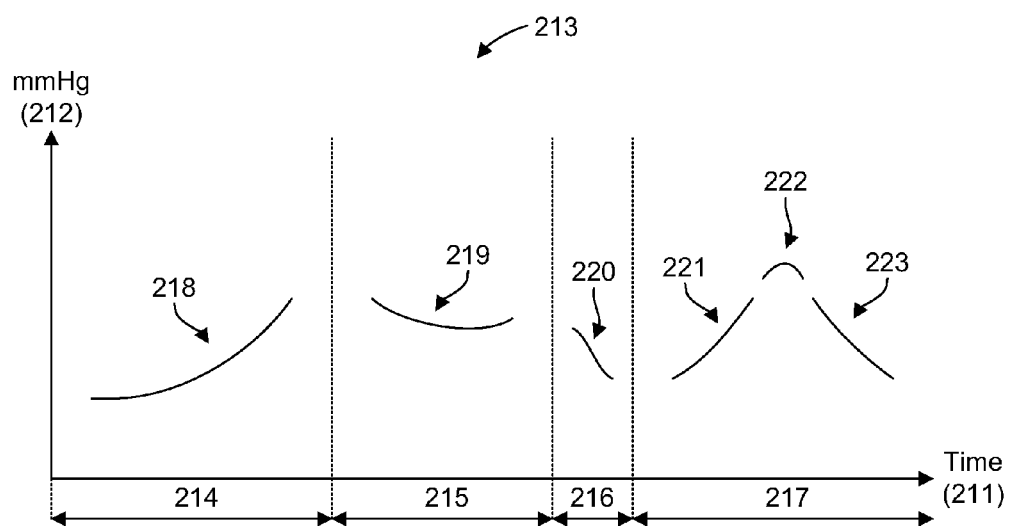
FIG. 9 is a graphical representations showing, by way of example, trend analysis of cardiac stroke volume profile.

FIG. 9 is a graphical representation showing, by way of example, trend analysis 213 of cardiac stroke volume profile. The x-axis represents time. The y-axis indicates stroke volume index in $ml/M^2$. Averaged changes in stroke volume index are plotted over time throughout each of four phases 214, 215, 216, 217 of a Valsalva maneuver.

Transcardiac Impedance Monitoring Method

Figure 10:
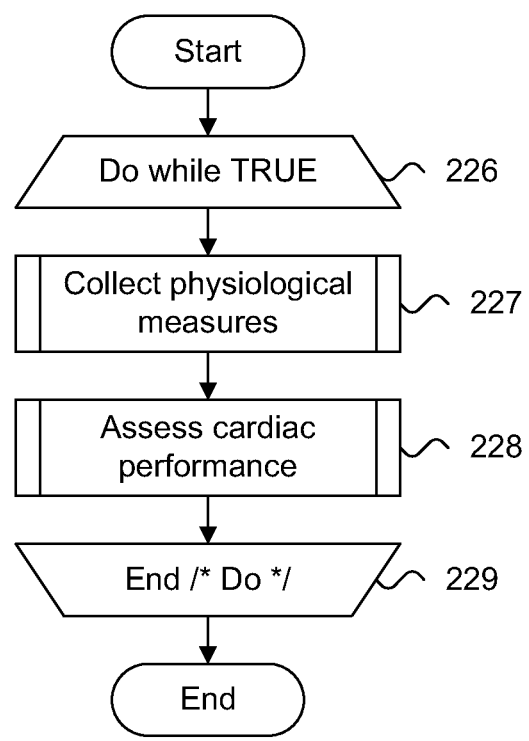
FIG. 10 is a flow chart showing a method for assessing cardiac performance through transcardiac impedance monitoring, in accordance with a further embodiment of the present invention.

FIG. 10 is a flow chart showing a method 225 for assessing cardiac performance through transcardiac impedance monitoring, in accordance with a further embodiment of the present invention. The method 225 is described as a sequence of process operations or steps, which can be executed, for instance, by a server 191 (shown in FIG. 7). In a further embodiment, the method 225 can be executed directly by the IMD 103, PMD 132, or related means, which generate a cardiac performance assessment 205 for retrieval by an external device.

The method 225 preferably executes as a continuous processing loop (blocks 226-229). During each iteration (block 226), the physiological measures 195 are retrieved from the IMD 103 and stored in the database 197, as further described below with reference to FIG. 11. Cardiac performance is then assessed (block 228), as further described below with reference to FIG. 12. Processing continues (block 229), until the method exits or terminates.

Collecting Physiological Measures

Figure 11:
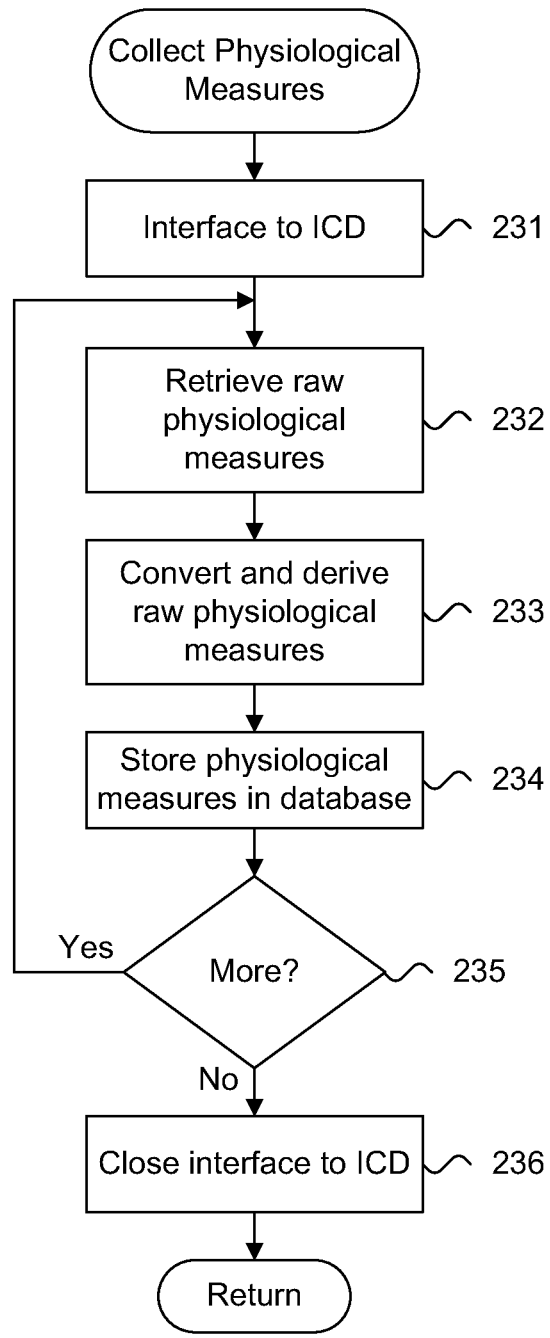
FIG. 11 is a flow chart showing a routine for collecting physiological measures for use in the method of FIG. 10.

FIG. 11 is a flow chart showing a routine 230 for collecting physiological measures for use in the method 225 of FIG. 10. The purpose of this routine is to regularly interface to the IMD 103, retrieve the physiological measures 195 and programming parameters 196, and store the retrieved physiological measures 195 and programming parameters 196 in the database 197.

The routine begins initially by interfacing to the IMD 103 (block 231), using, for instance, inductive or static magnetic means, as would be appreciated by one skilled in the art. Raw physiological measures 195 are retrieved from the IMD 103 (block 232). The raw physiological measures 195 are converted and derived into impedance measures 198, cardiac dimensional measures 199, LVEF measures 200, and LVEDP measures 201 (block 233). The physiological measures are stored in the database 197 (block 234). If further physiological measures 195 or programming parameters 196 require exchange with the IMD 103 (block 235), processing continues. Otherwise, the interface to the IMD 103 is closed (block 236), the routine returns.

Assessing Cardiac Performance

Figure 12:
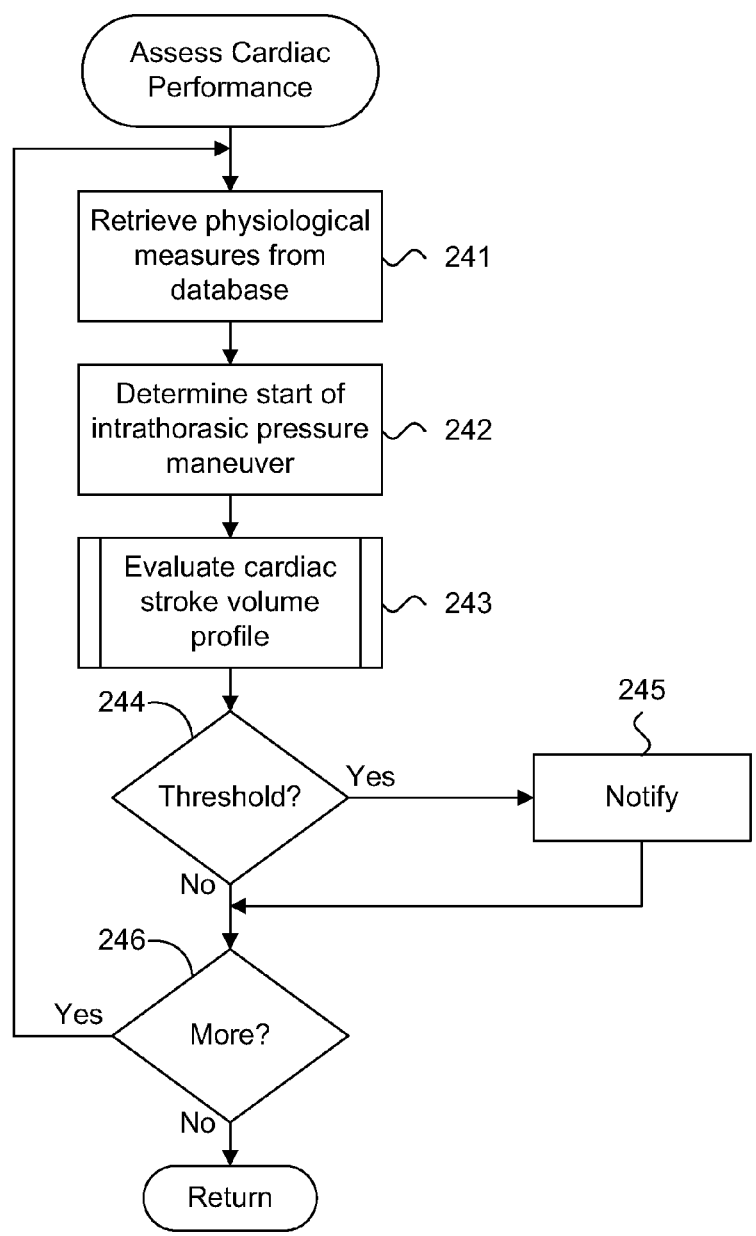
FIG. 12 is a flow chart showing a routine for assessing cardiac performance for use in the method of FIG. 10.

FIG. 12 is a flow chart showing a routine 240 for assessing cardiac performance for use in the method 225 of FIG. 10. The purpose of this routine is to periodically assess cardiac performance through an analysis of the cardiac stroke volume profile trends 224 (shown in FIG. 9).

As an initial step, physiological measures, including impedance measures 198, cardiac dimensional measures 199, LVEF measures 200, and LVEDP measures 201, are retrieved from the database 197 (shown in FIG. 7) (block 241). The start of the intrathoracic pressure maneuver under consideration is determined (block 242). In the described embodiment, the start of the intrathoracic pressure maneuver is determined by retrieving an explicit marker recorded by the patient 100 or by indirect means based upon an analysis of the retrieved physiological measures, as would be appreciated by one skilled in the art.

Next, the cardiac stroke volume profile 224 is evaluated to form a cardiac performance assessment 205 (block 243), further described below with reference to FIG. 13. If the cardiac performance assessment 205 exceeds the predefined threshold 204 (block 244), a notification is generated (block 245). In the described embodiment, the notification takes the form of generating an alert for review and possible action by healthcare providers and can include generating appropriate feedback to the patient 100, such as described in commonly-assigned U.S. Pat. No. 6,203,495, the disclosure of which is incorporated by reference.

If the cardiac performance assessment 205 does not exceed the threshold 204 (block 244), no notification is generated. If further retrieved physiological measures require evaluation (block 246), processing continues. Otherwise, the routine returns.

Evaluating Arterial Blood Pressure Profile Relative to Valsalva Maneuver

Figure 13:
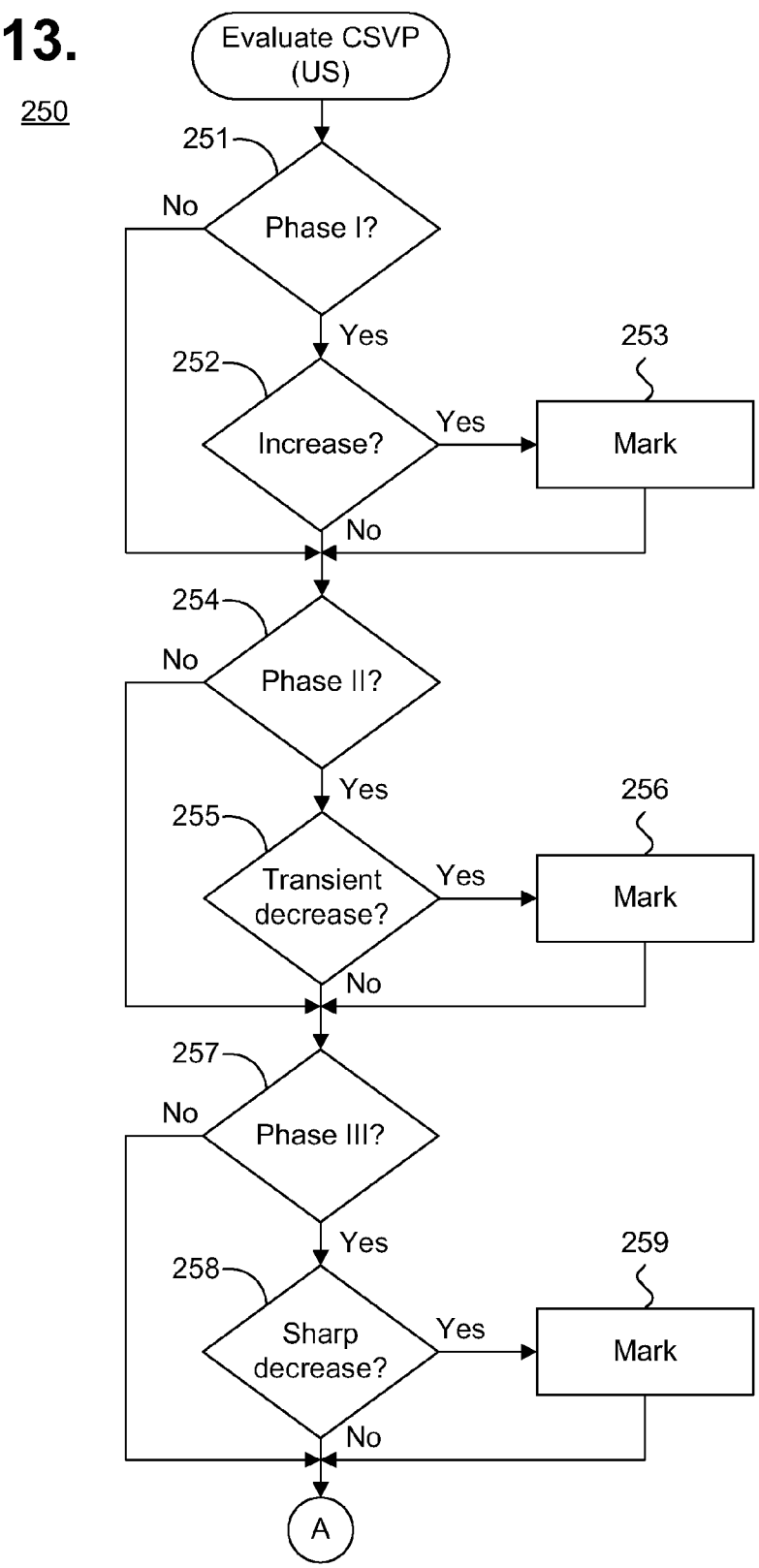
FIG. 13 is a flow chart showing a routine for evaluating cardiac stroke volume profile relative to, by way of example, the Valsalva maneuver, for use in the routine of FIG. 12.
Figure 13:
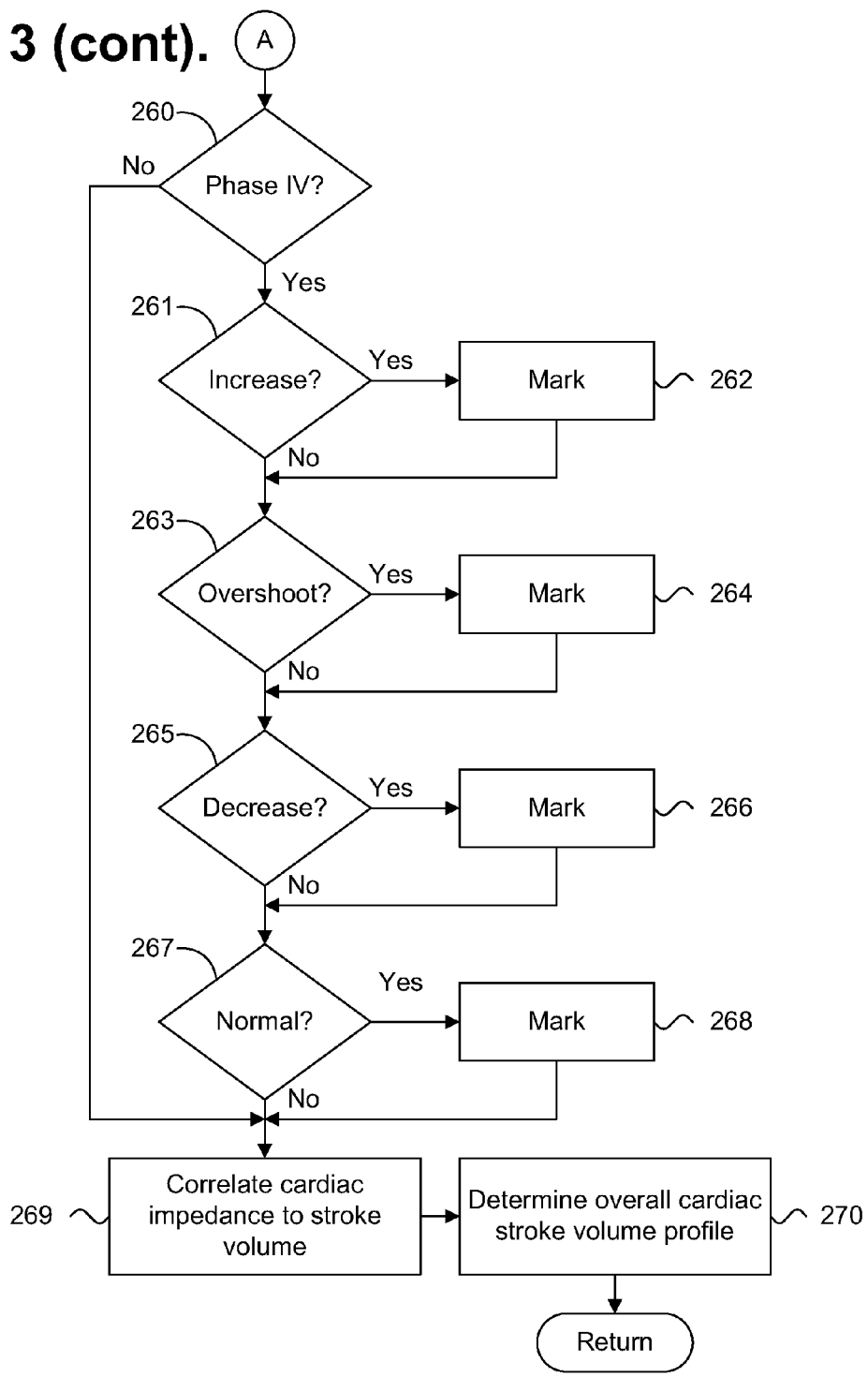

FIG. 13 is a flow chart showing a routine 250 for evaluating cardiac stroke volume profile 224 relative to, by way of example, the Valsalva maneuver, for use in the routine 240 of FIG. 11. The purpose of this routine is to generate a cardiac performance assessment 205 by forming a trend analysis of the retrieved physiological measures based on the phases of the Valsalva maneuver.

The trend analysis proceeds in four groups of steps (blocks 251-253, 254-256, 257-259, 260-268, respectively), which track each of the four phases of the Valsalva maneuver. During the first group, if the cardiac stroke volume profile 224 is in Phase I (block 251) and an increase in arterial pressure is apparent (block 252), the increase is marked (block 253). During the second group, if the cardiac stroke volume profile 224 is in Phase II (block 254) and a transient decrease in arterial pressure is apparent (block 255), the transient decrease is marked (block 256). During the third group, if the cardiac stroke volume profile 224 is in Phase III (block 256) and a significant decrease in arterial pressure is apparent (block 258), the significant decrease is marked (block 259). Finally, during the fourth group, if the cardiac stroke volume profile 224 is in Phase VI (block 260), four conditions are evaluated. If an increase in arterial pressure is apparent (block 261), the increase is marked (block 262). If the increase in arterial pressure is followed by an overshoot (block 263), the overshoot is marked (block 264). For the Valsalva maneuver, the overshoot is the strongest trend indication in the characteristic signature and indicates a healthy, non-heart failure person. If the overshoot is followed by a decrease in arterial pressure (block 265), the decrease is marked (block 266). Finally, if a resumption of normal arterial pressure is apparent (block 267), the resumption is marked (block 268).

Following the evaluation of each of the groups, the impedance measures are correlated to cardiac stroke volume to reflect cardiac dimensional changes, as described above with reference to FIGS. 4A-C. Next, the overall cardiac stroke volume profile 224 is determined (block 270) to generate a cardiac performance assessment 205. The cardiac performance assessment 205 quantifies the variants between the physiological measures determined during each of the phases against the cardiac stroke volume profile trends 224e-224h. Following determination of the cardiac performance assessment 205, the routine returns.

In the described embodiment, the cardiac impedance data can be analyzed in several ways. In one embodiment, a statistical analysis can be performed on impedance data to determine the mean impedance level and standard deviation over the entire response period. The mean $\overline{Z}$ and the standard deviation $S_z$ of the impedance data over the response period can be used as a cardiac performance assessment 205, where:

$$\overline{Z} = \frac{\sum Z_i}{n}$$

$$S_z = \sqrt{\frac{1}{N}\sum_{i=1}^{N}(Z_i - \overline{Z})}$$

In a further embodiment, a statistical analysis can be performed on different phases of the response period based on the collected impedance data to determine the cardiac performance assessment 205. For example, the mean and standard deviation analysis, described above, can be performed on physiological data from Phase IV of the response period relative to the performance of the Valsalva maneuver. The analyzed values reflect the amplitude of impedance change during the Valsalva maneuver as the cardiac performance assessment 205.

In a further embodiment, the impedance data can be analyzed for trends by calculating a linear regression over the collected data for Phase IV of the response period, such as described in Seborg et al., "Process Dynamics and Control," pp. 165-167 (John Wiley & Sons, 1989), the disclosure of which is incorporated by reference. By performing a linear regression, the response pattern during Phase IV can be fitted into a second-order system response, which is characterized by a transfer function, such as:

$$G(s) = \frac{K}{(\tau_1 s + 1)(\tau_2 s + 1)}$$

where $\tau_1$ and $\tau_2$ are derived empirically by linear regression. Alternatively, a second order process transfer function can arise upon transforming a second-order differential equation process model that has the general form of:

$$G(s) = \frac{K}{\tau^2 s^2 + 2\zeta\tau s + 1}$$

where $\zeta$ is the dimensionless damping factor.
By equating the two transfer functions, the value of the damping factor can be derived as:

$$\zeta = \frac{\tau_1 + \tau_2}{2\sqrt{\tau_1 \tau_2}}$$

The resulting response pattern is characterized by the derived value of the damping factor $\zeta$ according to the following table:

| | |
|---|---|
| $\zeta > 1$ | Over damped |
| $\zeta = 1$ | Critically damped |
| $0 < \zeta < 1$ | Under damped |

Phase IV of the Valsalva maneuver exhibits the most noticeable difference in cardiac response for the three groups of individuals described above with reference to FIGS. 4A-C and 5, that is, a healthy person, a patient suffering from heart disease and a patient suffering from heart failure. During Phase IV, the response pattern from the healthy person group closely resembles an under-damped second-order response, which is characterized by a damping factor between zero and one. The response pattern from the heart disease patient group closely resembles a critically-damped or under-damped second-order response, which is characterized by a damping factor that is equal to or greater than one but not substantially higher than one. The response pattern from the heart failure patient group shows no appreciable change, which resembles a severely-over damped system characterized by a large damping factor. The damping factor serves as a cardiac performance assessment 205. Other types of statistical analyses can also be performed, as would be recognized by one skilled in the art.

Heart Sound Profile

Figure 14:
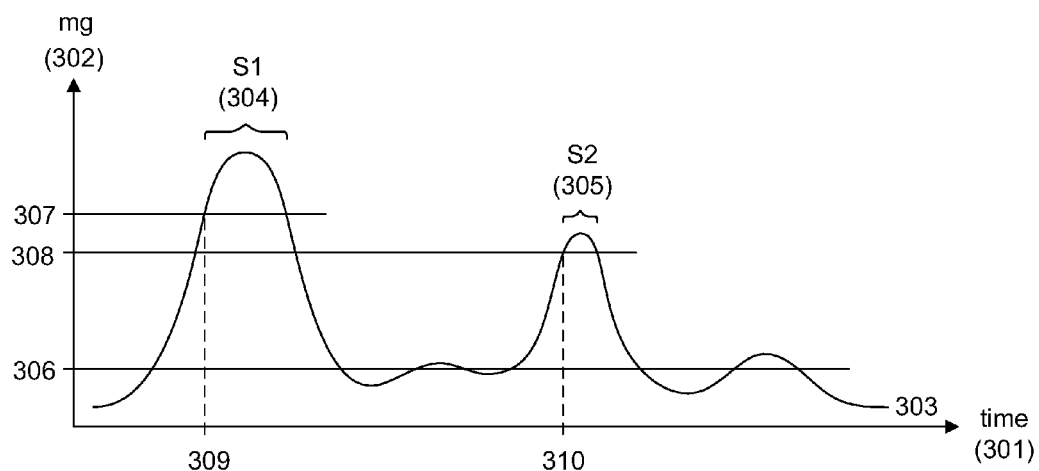
FIG. 14 is a graphical representation showing, by way of example, a heart sound profile.

FIG. 14 is a graphical representation showing, by way of example, a heart sound profile 303. The x-axis 301 represents time. The y-axis 302 represents acceleration units ($10^{-3}$ g, or milli-g).

In general, heart sounds are brief, discrete vibrations that can vary in intensity, frequency, timing, and quality. Four basic cardiac vibrations, or heart sounds, constitute heart events that can occur during each cardiac cycle. The first heart sound, referred to as 'S1,' identifies the onset of ventricular systole. The second heart sound, referred to as 'S2,' identifies the onset of diastole. The S1 and S2 heart sounds establish a framework within which other heart sounds, including third and fourth heart sounds, and murmurs are paced and timed.

An acoustic signal 303 for recorded heart sounds is plotted over time through a single cardiac cycle. For clarity, the acoustic signal 303 is shown as averaged values. The acoustic signal 303 represents acoustic energies generated by mechanical vibrations of the heart, both audible and inaudible. Generally, a single unaveraged or "raw" acoustic signal can be noisy. The acoustic signal can be processed through ensemble averaging, signal rectifying, low-pass or band-pass filtering, and similar signal processing operations to remove background noise 306 and other artifacts. Using the processed vibration signal, S1 heart sounds 304 and S2 heart sounds 305 can be respectively identified when thresholds 307, 308 are exceeded to mark heart sound starting points 309, 310. In a further embodiment, an adjustable timing window can be used to estimate the expected starting points of heart sounds, such as described in commonly-assigned U.S. Patent application Publication No. 20050148896, published Jul. 7, 2005, pending, the disclosure of which is incorporated by reference. In addition to vibration signal strength, heart sounds can further be represented by frequency or pitch, quality or timbre, and other representations plotted as a function of time or change.

Relationship of S1 Heart Sound to LV dP/dt

Figure 15:
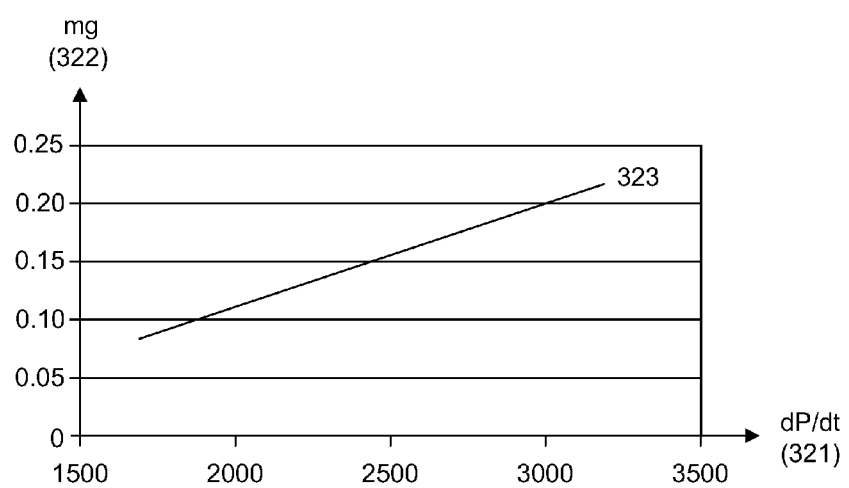
FIG. 15 is a graphical representation showing, by way of example, the relationship of an S1 heart sound to the rate of rise of left ventricular (LV) pressure LV dP/dt.

FIG. 15 is a graphical representation showing, by way of example, the relationship 323 of an S1 heart sound to the rate of rise of left ventricular (LV) pressure LV dP/dt. The x-axis 321 represents LV dP/dt in mm Hg/sec. The y-axis 322 represents acceleration units, or acoustic energy units.

The audible components of the S1 heart sound originate in the closing movement of the atrioventricular valves. The S1 heart sound includes two major components associated with the mitral and tricuspid valves. The mitral valve component coincides with the closure of the mitral valve, that is, the complete coaptation of leaflets. The intensity of the first heart sound depends upon LV contractility because increased contractility leads to a increased deceleration of blood by the tensed mitral valve, which in turn results in increased vibrations of the cardiohemic system. Thus, the vibration energy 323 of an S1 heart sound is proportionate to the rate of rise of LV pressure. The rate of rise of LV pressure is an isovolumetric phase index for evaluating left ventricular systolic performance. Additionally, LV dP/dt is also sensitive to changes in ventricular preload, such as described in E. Braunwald, Ed., "Heart Disease—a Textbook of Cardiovascular Medicine," Ch. 14, pp. 421-444, W.D. Saunders Co. (1997), the disclosure of which is incorporated by reference. Ventricular preload may be measured directly, or indirectly by several possible means, such as cardiac volumes, cardiac pressures, or S3 heart sounds. In one embodiment, such measures may be used to correct the S1 heart sound intensity for preload variations, such as described in commonly-assigned U.S. patent application Ser. No. 11/208,281, filed Aug. 19, 2005, pending, the disclosure of which is incorporated by reference. For example, during forced expiratory effort, the extent of decrease in S3 amplitude may be used to determine the LV filling pressure and correct the LV dP/dt measurement for changes in preload, such as described in commonly-assigned U.S. patent application Ser. No. 11/189,462, filed Jul. 26, 2005, pending, the disclosure of which is incorporated by reference. Vascular cardiac performance is significantly dependent on left ventricular function, specifically LV dP/dt and LVEF.

Figure 16:
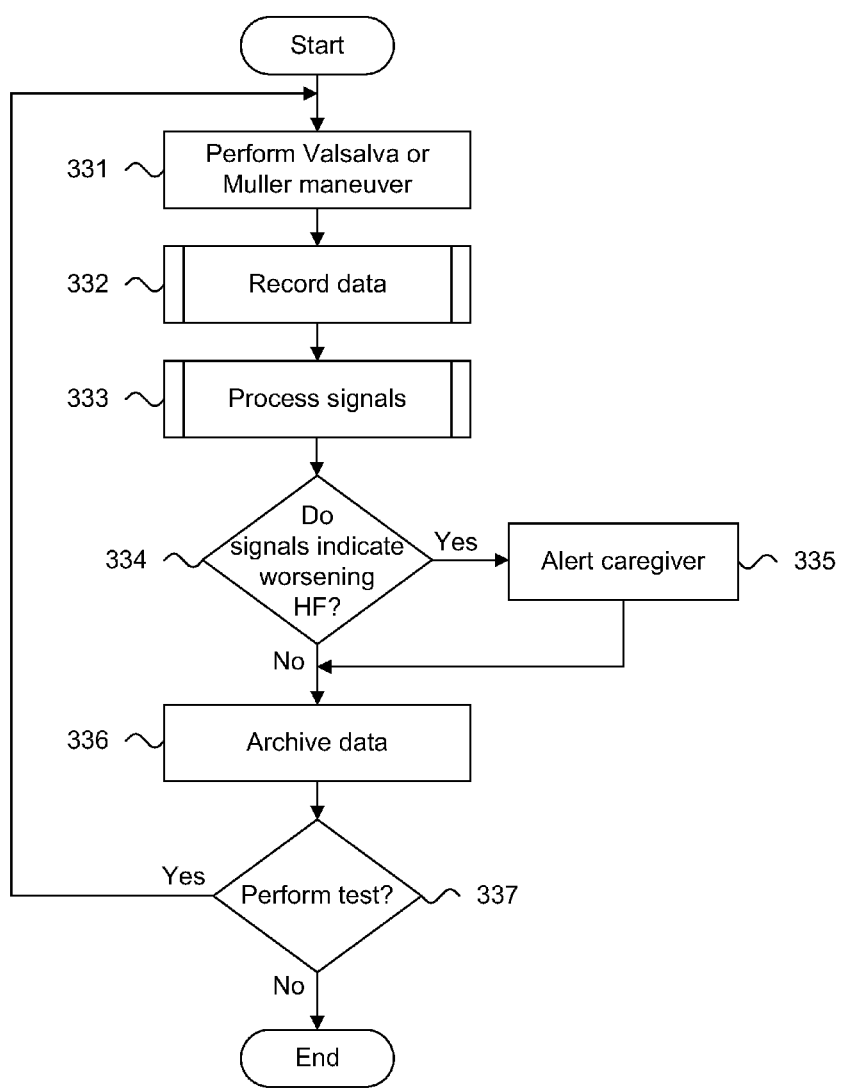
FIG. 16 is a flow chart showing a method for assessing cardiac performance through cardiac vibration monitoring, in accordance with a further embodiment.

FIG. 16 is a flow chart showing a method 330 for assessing cardiac performance through cardiac vibration monitoring, in accordance with a further embodiment. Method 330 is described as a sequence of process operations or steps, which can be executed, for instance, by a server 191 (shown in FIG. 7). In a further embodiment, the method 330 can be executed directly by the IMD 103, PMD 132, or related means, which generate a cardiac performance assessment 205 for retrieval by an external device.

Initially, cardiac performance is assessed by having the patient perform an intrathoracic pressure maneuver, such as the Valsalva or Müller maneuver (block 331), during which patient data is recorded (block 332) and signals are processed (block 333), as further described below respectively with reference to FIGS. 17 and 18. If the signals indicate a worsening of a heart failure condition (block 334), the responsible healthcare provider or caregiver is alerted (block 335). Worsening can be indicated by signal morphology or amplitude. Worsening could also be indicated by signature components, such as differences in response to performing an intrathoracic pressure maneuver or changes from historical responses. The signals can be evaluated through standard means square analysis and similar forms of signal processing. In addition to identifying a worsening of a heart failure condition, other forms of physiological changes can be detected, including identifying a trend indicating an onset, progression, regression, absence, or status quo of a heart failure condition. As well, the necessity of therapy changes can optionally be evaluated and, if necessary, initiated (block 334), such as described in commonly-assigned U.S. Patent application Publication No. 20030097158, published on May 22, 2003, pending, the disclosure of which is incorporated by reference. The data is archived (block 337) and, if necessary, cardiac performance can be re-assessed by performing the test again (block 337). Otherwise, the method exits or terminates.

Recording Data

Figure 17:
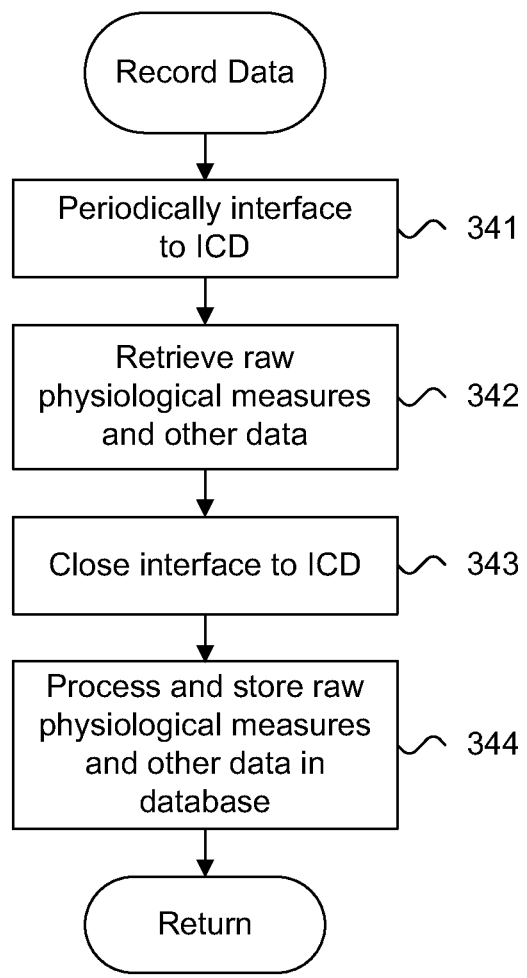
FIG. 17 is a flow chart showing a routine for recording data for use in the method of FIG. 16.

FIG. 17 is a flow chart showing a routine 340 for recording data for use in the method 340 of FIG. 16. The purpose of this routine is to periodically interface to the IMD 103, retrieve the physiological measures 195, programming parameters 196, and other data, and store the retrieved information in the database 197.

The routine begins initially by periodically interfacing to IMD 103 (block 341), using, for instance, inductive or radio frequency telemetry. Raw physiological measures 195 and other data are retrieved from the IMD 103 (block 343). The interface to the IMD 103 is closed (block 343). The raw physiological measures 195 and other data are processed and stored in the database 197 (block 344). Processing can include ensemble averaging, signal rectifying, low-pass or band-pass filtering, and similar signal processing operations to improve the intensity, frequency, or quality of the resulting cardiac vibration measures. The routine then returns.

Processing Signals

Figure 18:
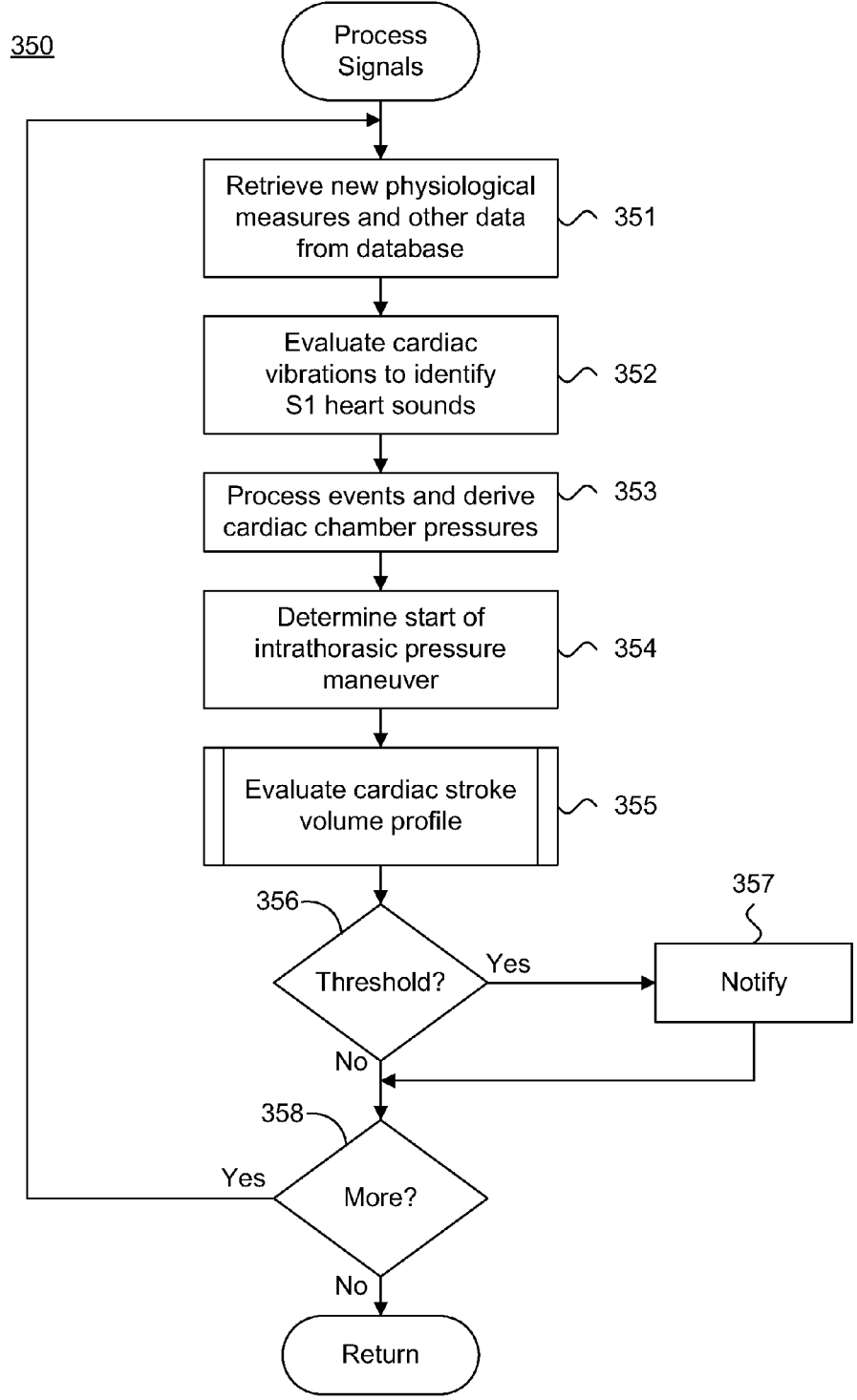
FIG. 18 is a flow chart showing a routine for processing signals for use in the method of FIG. 16.

FIG. 18 is a flow chart showing a routine 350 for processing signals for use of the method 330 of FIG. 16. The purpose of this routine is to periodically assess cardiac performance through an analysis of cardiac stroke volume profile trends 224 (shown in FIG. 9).

As an initial step, raw physiological measures 195 and other data is retrieved from the database 197 (block 351). Cardiac vibrations, including auscultatory, sub-audible, and various forms of detectable cardiac events, including S1 heart sounds, are identified (block 352), such as by applying a threshold 307 to a cardiac vibratory signal, to identify the onset of ventricular systole. The cardiac vibrations are processed and cardiac pressures are derived (block 353). Event processing can include determining amplitude and frequency spectrum parameters for S1 heart sound intensity and the ratioing of S1 heart sounds with other cardiac preload parameters, such as S1 heart sound energy to total energy and S1 heart sound intensity to pulmonary artery pressure, such as described in commonly-assigned U.S. patent application Ser. No. 11/208,281, filed Aug. 19, 2005, pending, the disclosure of which is incorporated by reference. Other parameters and cardiac preload ratios are possible. In addition, the magnitude, rate of change, and rise and fall times of each parameter can be derived. In particular, cardiac chamber pressures, in particular, LVEF and LVEDP, can be derived by proportionately extrapolating S1 heart sound intensity to the rate of rise of LV pressure, such as described above with reference to FIG. 15.

The start of the intrathoracic pressure maneuver under consideration is determined (block 354). In one embodiment, the start of the intrathoracic pressure maneuver is determined by retrieving an explicit marker recorded by the patient 100 or by indirect means based upon an analysis of the retrieved physiological measures. In a further embodiment, the start of the intrathoracic pressure maneuver is determined with the assistance of an external medical device 122, such as a pressure monitor or a thoracic pressure electrode, such as described above with reference to FIG. 2.

Next, the cardiac stroke volume profile 224 is evaluated to form a cardiac performance assessment 205 (block 355), further described above with reference to FIG. 13. If the cardiac performance assessment 205 exceeds the predefined threshold 204 (block 356), a notification is generated (block 357). In one embodiment, the notification takes the form of generating an alert for review and possible action by healthcare providers and can include generating appropriate feedback to the patient 100, such as described in commonly-assigned U.S. Pat. No. 6,203,495, the disclosure of which is incorporated by reference.

If the cardiac performance assessment 205 does not exceed the threshold 204 (block 356), no notification is generated. If further retrieved physiological measures require evaluation (block 358), processing continues. Otherwise, the routine returns.

While the invention has been particularly shown and described as referenced to the embodiments thereof, those skilled in the art will understand that the foregoing and other changes in form and detail may be made therein without departing from the spirit and scope of the invention.

What is claimed is:

1. A system for evaluating cardiac performance relative to performance of an intrathoracic pressure maneuver, comprising:
   an implantable medical device to indirectly sense heart sounds by directly collecting cardiac vibration measures; and
   an analysis component to evaluate cardiac functional changes to the heart sounds in response to performance of an intrathoracic pressure maneuver, wherein ventricular preload is measured to correct S1 heart sound intensity for preload variations.

2. A system according to claim 1, further comprising:
   an evaluation component to evaluate the heart sounds to derive cardiac chamber pressure, wherein the cardiac chamber pressure comprises at least one of left ventricular ejection fraction, left ventricular end diastolic pressure, pulmonary capillary wedge pressure, pulmonary artery pressure, and an S3 index of pressure.

3. A system according to claim 1, wherein the implantable medical device comprises at least one of a cardiac pacemaker, cardioverter defibrillator, cardiac resynchronization device, cardiovascular monitor, and therapeutic device monitoring and treating structural problems of the heart.

4. A system according to claim 1, wherein heart sounds comprising cardiac events for at least one of intensity of a first heart sound, ratio of first heart sound energy to total energy, and ratio of first heart sound intensity to pulmonary artery pressure are determined.

5. A system according to claim 1, wherein the intrathoracic pressure maneuver comprises at least one of a Valsalva and Müller maneuver.

6. A system according to claim 1, further comprising:
   at least one of:
      an evaluation subcomponent to evaluate at least one of overdamping and underdamping cardiac impedance response relative to normative levels; and
      a notification subcomponent to generate a notification responsive to the at least one of overdamping and underdamping cardiac impedance response.

7. A system according to claim 1, wherein thoracic pressure is monitored during the intrathoracic pressure maneuver, further comprising:
   an external pressure monitor to define a confined volume configured to receive at least one of a forced exhalation and a forced inhalation and to measure the thoracic pressure relative to the confined volume.

8. A system according to claim 1, wherein the cardiac vibrations are selected from the group comprising auscultatory, sub-audible, and detectable cardiac events.

9. A method for evaluating cardiac performance relative to performance of an intrathoracic pressure maneuver, comprising:
   indirectly sensing heart sounds by directly collecting cardiac vibration measures through an implantable medical device;
   a processor evaluating cardiac functional changes to the heart sounds in response to performance of an intrathoracic pressure maneuver; and
   measuring ventricular preload to correct S1 heart sound intensity for preload variations.

10. A method according to claim 9, further comprising:
evaluating the heart sounds to derive cardiac chamber pressure, wherein the cardiac chamber pressure comprises at least one of left ventricular ejection fraction, left ventricular end diastolic pressure, pulmonary capillary wedge pressure, pulmonary artery pressure, and an S3 index of pressure.

11. A method according to claim 9, wherein the medical device comprises at least one of a cardiac pacemaker, cardioverter defibrillator, cardiac resynchronization device, cardiovascular monitor, and therapeutic device monitoring and treating structural problems of the heart.

12. A method according to claim 9, further comprising:
determining heart sounds comprising cardiac events for at least one of intensity of a first heart sound, ratio of first heart sound energy to total energy, and ratio of first heart sound intensity to pulmonary artery pressure.

13. A method according to claim 9, wherein the intrathoracic pressure maneuver comprises at least one of a Valsalva and Müller maneuver.

14. A method according to claim 9, further comprising:
performing at least one of:
evaluating at least one of overdamping and underdamping cardiac impedance response relative to normative levels; and
generating a notification responsive to the at least one of overdamping and underdamping cardiac impedance response.

15. A method according to claim 9, further comprising:
monitoring thoracic pressure during the intrathoracic pressure maneuver;
defining a confined volume configured to receive at least one of a forced exhalation and a forced inhalation; and
measuring the thoracic pressure relative to the confined volume.

16. A method according to claim 9, wherein the cardiac vibrations are selected from the group comprising auscultatory, sub-audible, and detectable cardiac events.

17. A non-transitory computer-readable storage medium holding code for performing the method of claim 9.

18. A system for evaluating cardiac performance relative to performance of an intrathoracic pressure maneuver, comprising:
an implantable medical device to indirectly sense heart sounds by directly collecting cardiac vibration measures; and
an analysis component to evaluate cardiac functional changes to the heart sounds in response to performance of an intrathoracic pressure maneuver, wherein thoracic pressure is monitored during the intrathoracic pressure maneuver; and
an external pressure monitor to define a confined volume configured to receive at least one of a forced exhalation and a forced inhalation and to measure the thoracic pressure relative to the confined volume.

19. The system of claim 18, wherein ventricular preload is measured to correct S1 heart sound intensity for preload variations.

* * * * *